US008535887B2

(12) United States Patent
Bertelsen et al.

(10) Patent No.: US 8,535,887 B2
(45) Date of Patent: Sep. 17, 2013

(54) GENETIC MARKERS ASSOCIATED WITH INTERFERON-ALPHA RESPONSE

(75) Inventors: Arthur Bertelsen, Ridgewood, NJ (US); Jacques Fellay, Durham, NC (US); Dongliang Ge, Raleigh, NC (US); David B. Goldstein, Durham, NC (US); John G. McHutchison, Chapel Hill, NC (US); Ping Qiu, Edison, NJ (US); Kevin Shianna, Durham, NC (US); Jason S. Simon, Westfield, NJ (US); Alexander J. Thompson, Durham, NJ (US); Thomas Urban, Durham, NC (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 518 days.

(21) Appl. No.: 12/785,060

(22) Filed: May 21, 2010

(65) Prior Publication Data
US 2010/0297080 A1 Nov. 25, 2010

Related U.S. Application Data

(60) Provisional application No. 61/180,320, filed on May 21, 2009, provisional application No. 61/223,169, filed on Jul. 6, 2009, provisional application No. 61/232,547, filed on Aug. 10, 2009.

(51) Int. Cl.
*C12Q 1/70* (2006.01)
*C12Q 1/68* (2006.01)
(52) U.S. Cl.
USPC ............... 435/6.11; 435/5; 435/6.1; 435/6.12
(58) Field of Classification Search
None
See application file for complete search history.

(56) References Cited

U.S. PATENT DOCUMENTS

| 2005/0014159 A1 | 1/2005 | Chen et al. |
| 2010/0316608 A1 | 12/2010 | Suppiah et al. |

FOREIGN PATENT DOCUMENTS

| EP | 1136571 | 9/2001 |
| WO | WO2007/029041 | 3/2007 |
| WO | WO2009/046369 | 4/2009 |
| WO | WO2009/060066 | 5/2009 |
| WO | WO2010/025380 | 3/2010 |

OTHER PUBLICATIONS

Rauch et al. Genetic Variation in IL28B is Associated with Chronic Hepatitis C and Treatment Failure: A Genome-Wide Assocation Study. Gastroenterology. 2010: 138: p. 1338-1345.*
Persico et al. Elevated expression and polymorphisms of SOCS3 influence patient response to antiviral therapy in chronic hepatitis C. Gut 2008: 57: 507-515.*
Jacobsen, Ira M., et al.; "Peginterferon alfa-2b and Weight-Based or Flat-Dose Ribavirin in chronic Hepatitis C Patients: A Randomized Trial"; Hepatology; 46(4):971-981 (2007).
NCBI Database SNP DB [Online] Reference SNP (RefSNP) Cluster Report: rs12979860 (Jun. 1, 2004).
Schott, E., et al.; "Association of TLR7 Polymorphisms with Response to Interferon-Alpha Therapy in Patients with Chronic HCV Infection"; Journal of Hepatology; 46:S176 (2007).
Tanaka, Yasuhito, et al.; "Genome-wide association of IL28B with response to pegylated interferon-α and ribavirin therapy for chronic hepatitis C"; Nature Genetics; 41(10):1105-1109 (2009); Published online Sep. 13, 2009, doi:10.1038/ng 449.
Thomas, David L., et al.; "Genetic variation in IL28B and spontaneous clearance of hepatitis C virus"; Nature; 461(7265):798-801 (2009).
Written Opinion of the International Searching Authority for International Application No. PCT/US2010/035782 dated Nov. 2, 2010.
Ge, Dongliang, et al.; "Genetic variation in IL28B predicts hepatitis C treatment-induced viral clearance"; 461(7262):399-401 (Sep. 17, 2009); Published online Aug. 16, 2009, doi:10.1038/nature08309 Letter.
International Search Report for International Application No. PCT/US2010/035782 dated Nov. 2, 2010.
Jacobsen, Ira M., et al; "Peginterferon alfa-2b and Weight-Based or Flat-Dose Ribavirin in chronic Hepatitis C Patients: A Randomized Trial"; Hepatology; 46(4):971-981 (2007).
McCone, Jonathan, et al; "Sustained Virologic Response (SVR) and Predictors of Response in African American (AA) Patients in the Ideal (Individualized Dosing Efficacy Versus Flat Dosing to Assess Optimal Pegylated Interferon Therapy) Phase 3B Study"; Hepatology; 48(4):430A-431A.
NCBI Database SNP DD [Online] Reference SNP (RefSNP) Cluster Report: rs12979860 (Jun. 1, 2004).
NCBI Database GenBank [Online] Swiss-Prot Accession No. Q8IZI9.2 (Oct. 5, 2010).
Reid, Andrea E.; "Viral Hepatitis in African Americans"; Curr. Hepatitis Rep.; 7(3):120-126 (2008).
Schott, E., et al.; "Association of TLR7 Polymorphisms with Response to Interferon-Alpha-Based Therapy in Patients with Chronic HCV Infection"; Journal of Hepatology; 46:S176 (2007).
Starkel, Peter; "Genetic Factors predicting response to interferon treatment for viral hepatitis C"; Gut; 57(4):440-442 (2008).
Suppiah, Vijayaprakash, et al.; "IL28B is associated with response to chronic hepatitis C interferon-α and ribavirin therapy"; Nature Genetics; 41(10):1100-1104 (2009); Published online: Sep. 13, 2009, doi:10.1038/ng.447.
Tanaka, Yasuhito, et al; "Genome-wide association of IL28B with response to pegylated interferon-α and ribavirin therapy for chronic hepatitis C"; Nature Genetics; 41(10):1105-1109 (2009); Published online Sep. 13, 2009, doi:10.1038/ng 449.
Thomas, David L., et al.; "Genetic variation in IL28B and spontaneous clearance of hepatitis C virus"; Nature; 461(7265):798-801(2009).
Written Opinion of the International Searching Authority for International Application No. PCTMS2010/035782 dated Nov. 2, 2010.

* cited by examiner

*Primary Examiner* — Michelle S Horning

(57) ABSTRACT

The present invention provides genetic markers on human chromosome 19 that are associated with a beneficial response to interferon alpha (IFN-α). These IFN-α response markers are useful, inter alia, to identify patients who are most likely to benefit from treatment with IFN-α pharmaceutical compositions and drug products, in methods of treating patients having a disease susceptible to treatment with an IFN-α, and in methods for selecting the most appropriate therapy for such patients.

7 Claims, 5 Drawing Sheets

```
  1 mtgdcmpvlv lmaavltvtg avpvarlrga lpdargchia qfkslspqel qafkrakdal
         t                  h
 61 eeslllkdck crsrlfprtw dlrqlqvrer pvaleaelal tlkvleatad tdpalgdvld
             r
121 qplhtlhhil sqlraciqpq ptagprtrgr lhhwlhrlqe apkkespgcl easvtfnlfr
                                                                   k
181 lltrdlncva sgdlcv
```

Figure 4

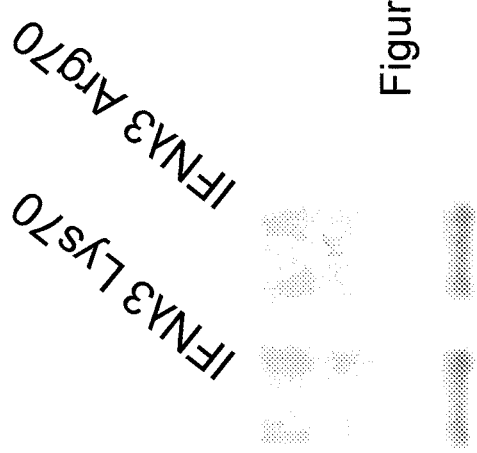
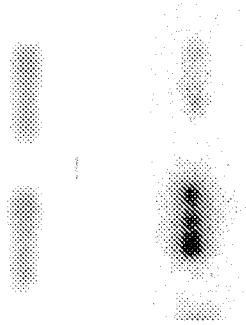
Figure 5A
Figure 5B

SEQUENCE LISTING

```
<160> NUMBER OF SEQ ID NOS: 10

<210> SEQ ID NO 1
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: Y indicates C or T

<400> SEQUENCE: 1
ctgaaccagg gagctccccg aaggcgygaa ccagggttga attgcactcc gc            52

<210> SEQ ID NO 2
<211> LENGTH: 52
<212> TYPE: DNA
<213> ORGANISM: Homo sapiens
<220> FEATURE:
```

```
<221> NAME/KEY: misc_feature
<222> LOCATION: (27)..(27)
<223> OTHER INFORMATION: S indicates G or C

<400> SEQUENCE: 2
cagagagaaa gggagctgag ggaatgsaga ggctgcccac tgagggcagg gg        52

<210> SEQ ID NO 3
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: Y indicates C or T

<400> SEQUENCE: 3
tcctggggaa gaggcgggag cggcacytgc agtccttcag cagaagcgac tc        52

<210> SEQ ID NO 4
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: R indicates G or A

<400> SEQUENCE: 4
ctgagagaag tcaaattcct agaaacrgac gtgtctaaat atttgccggg gt        52

<210> SEQ ID NO 5
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: K = G or T

<400> SEQUENCE: 5
cttttgtttt cctttctgtg agcaatktca cccaaattgg aaccatgctg ta        52

<210> SEQ ID NO 6
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: M = A or C

<400> SEQUENCE: 6
agaacaaatg ctgtatgatt ccccctmcat gaggtgctga gagaagtcaa at        52

<210> SEQ ID NO 7
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: M = A or C

<400> SEQUENCE: 7
tattcatttt tccaacaagc atcctgmccc aggtcgctct gtctgtctca at        52

<210> SEQ ID NO 8
```

-continued

```
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: R indicates G or A

<400> SEQUENCE: 8
cctaaatatg atttcctaaa tcatacrgac atatttcctt gggagctata ca         52

<210> SEQ ID NO 9
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: Y indicates C or T

<400> SEQUENCE: 9
tcatataaca atatgaaagc cagagayagc tcgtctgaga cacagatgaa ca         52

<210> SEQ ID NO 10
<211> LENGTH: 196
<212> TYPE: PRT
<213> ORGANISM: Homo sapiens

<400> SEQUENCE: 10
```

Met Thr Gly Asp Cys Met Pro Val Leu Val Leu Met Ala Ala Val Leu
 1               5                  10                  15

Thr Val Thr Gly Ala Val Pro Val Ala Arg Leu Arg Gly Ala Leu Pro
            20                  25                  30

Asp Ala Arg Gly Cys His Ile Ala Gln Phe Lys Ser Leu Ser Pro Gln
        35                  40                  45

Glu Leu Gln Ala Phe Lys Arg Ala Lys Asp Ala Leu Glu Glu Ser Leu
    50                  55                  60

Leu Leu Lys Asp Cys Lys Cys Arg Ser Arg Leu Phe Pro Arg Thr Trp
65                  70                  75                  80

Asp Leu Arg Gln Leu Gln Val Arg Glu Arg Pro Val Ala Leu Glu Ala
                85                  90                  95

Glu Leu Ala Leu Thr Leu Lys Val Leu Glu Ala Thr Ala Asp Thr Asp
            100                 105                 110

Pro Ala Leu Gly Asp Val Leu Asp Gln Pro Leu His Thr Leu His His
        115                 120                 125

Ile Leu Ser Gln Leu Arg Ala Cys Ile Gln Pro Gln Pro Thr Ala Gly
    130                 135                 140

Pro Arg Thr Arg Gly Arg Leu His His Trp Leu His Arg Leu Gln Glu
145                 150                 155                 160

Ala Pro Lys Lys Glu Ser Pro Gly Cys Leu Glu Ala Ser Val Thr Phe
                165                 170                 175

Asn Leu Phe Arg Leu Leu Thr Arg Asp Leu Asn Cys Val Ala Ser Gly
            180                 185                 190

Asp Leu Cys Val
        195

GENETIC MARKERS ASSOCIATED WITH INTERFERON-ALPHA RESPONSE

FIELD OF THE INVENTION

The present invention relates to genetic markers on human chromosome 19 that are predictive of a beneficial response to therapy with an interferon alpha.

BACKGROUND OF THE INVENTION

Identification of any publication in this section or any section of this application is not an admission that such publication is prior art to the present invention.

The type I interferon alpha (IFN-α) family of proteins exhibit clinically important antiviral, antiproliferative and immunomodulatory activities, and various IFN-α, proteins have been approved for treating a variety of diseases, including hepatitis and cancers. Due to the short plasma half-life of the originally approved IFN-α proteins, longer-acting versions have been developed: in particular, peginterferon alfa-2a, marketed by Hoffman-La Roche (Nutley, N.J.) under the trade name PEGASYS®; peginterferon alfa-2b, marketed by Schering-Plough (Kenilworth, N.J.) under the trade name PegIntron®; and Albuferong, a fusion between human serum albumin and interferon alpha-2b, which is in late-stage clinical development by Human Genome Sciences.

IFN-α proteins affect a variety of cellular functions, including DNA replication and RNA and protein synthesis, in both normal and abnormal cells. Thus, cytotoxic effects of IFN-α therapy are not restricted to tumor or virus infected cells but are also manifested in normal, healthy cells as well. As a result, undesirable, but typically reversible, side effects arise during IFN-α therapy, particularly when high doses are required to achieve a therapeutic effect. For example, administration of IFN-α proteins can lead to reduced red blood cell, white blood cell and platelet counts, and high doses commonly produce flu-like symptoms (e.g., fever, fatigue, headaches and chills), gastrointestinal disorders (e.g., anorexia, nausea and diarrhea), mood changes and alteration of liver enzymes.

Such side effects can be particularly of concern due to the long treatment times typically required with IFN-α-based therapy. For example, the recommended duration of peginterferon alfa/ribavirin combination therapy for hepatitis C virus (HCV) infection is between 24 and 48 weeks, depending on HCV genotype and baseline viral load. The treatment duration for certain cancer indications may be even longer, as evidenced by a recently completed clinical trial of peginterferon alfa-2b as adjuvant therapy for resected stage III melanoma, in which the patients were treated with 6 µg/kg peginterferon alfa-2b a week subcutaneously for 8 weeks (induction phase), followed by 3 µg/kg per week subcutaneously for an intended treatment duration of 5 years (maintenance phase) (Eggermont A. M. M. et al., *Lancet* 372:117-126 [2008]).

In addition to the potential for problematic side effects, the therapeutic effect of IFN-α therapy cay vary widely among patients with a particular disease. For example, combination peginterleron alfa-2b/ribavirin therapy for HCV produces a sustained viral response (SVR) rate of between approximately 20% and 93% in various patient groups defined by HCV genotype and baseline viral load. Also, HCV patients of African ancestry have significantly lower sustained viral response (SVR) rates than patients of European ancestry. See, e.g., McCone, et al., *Hepatology* 48(4):430A-431A, Abstr. No. 268 (59th Ann. Mtg. Am. Assoc. Study Liver Dis., AASLD, San Francisco, Calif., USA, Oct. 31-Nov. 4, 2008); Reid, A. E., *Curr. Hepatitis Rep.*, Vol. 7, No. 3, pp. 120-126 (2008); Jacobson, I. M. et al. Hepatology 46 (4): 971-981 (2007). Similarly, Eggermont et al., supra, reported better clinical outcomes for patients with earlier stage III melanoma than for patients with later stage disease, in particular an overall risk reduction of relapse of approximately 18-25%.

Thus, in view of the side effect and variable response and sensitivity profiles observed with IFN-α therapy, a need exists for a way of identifying patients who are most likely to benefit from IFN-α therapy. The present invention addresses this need.

SUMMARY OF THE INVENTION

The present invention is based on the discovery that several single nucleotide polymorphisms (SNPs) on human chromosomal region 19q13.13 are strongly associated with response to peginterferon alfa/ribavirin treatment in patients chronically infected with HCV genotype 1.

One of these SNPs is a C/T polymorphism, identified as rs12979860 in the NCBI SNP Database. The rs12979860 polymorphism is located 3 kb upstream of the interleukin 28B (IL-28B) gene, which encodes interferon lambda 3 (IFN-λ3). The presence of the C allele is associated with a better treatment response, with the C/C genotype associated with a 2-fold, 3-fold, and 2-fold better sustained viral response (SVR) than the T/T genotype in HCV patients of European, African and Hispanic ancestry, respectively. Moreover, since the C/C genotype is present at a substantially higher frequency in a population of European ancestry than in a population of African ancestry, the rs12979860 polymorphism explains a significant component of the inter-population difference in the response of HCV patients to pegylated interferon alpha/ribavirin combination therapy. The frequency of the rs1279860 C allele is significantly reduced in a cohort of patients chronically infected with HCV compared to a randomly selected population sample with unknown hepatitis C status, suggesting that the C allele is also associated with a greater probability of natural clearance of hepatitis C genotype 1.

The inventors herein also identified associations between rs12979860 and other SNPs on 19q13.13, which themselves are associated with SVR. Two of these SNPs are in the IL-28B gene: rs28416813, a G/C polymorphism located 37 bases upstream of the ATG start codon and rs8103142, an A/G polymorphism located in the coding sequence that results in the presence of an amino acid polymorphism of Lys or Arg at amino acid position 70 of the IFN-λ3 amino acid sequence shown in FIG. 4 (SEQ ID NO:10). The A allele of the rs8103142 polymorphism encodes Lys at position 70 of IFN-λ3 whereas the G polymorphism results in Arg at position 70. Based on a recently published crystal structure of IFN-λ3 (Gad, H. H. et al., IBC 2009, published online on May 20, 2009 as Manuscript M109.002923), the inventors herein believe that the Arg/Lys variation occurs in the AB loop, a region that is likely involved in binding of IFN-λ3 to IFN-λR1.

The SNPs in the IL28B gene are of particular interest as candidate causal polymorphisms since IFN-λ3 expression is induced by infection with HCV and other viruses, and IFN-λ3 exhibits antiviral activity in vivo (Sheppard, P et al., *Nature Immunol.* 4(1):63-68 (2003); Kotenko, S. V., et al., *Nature Immunology* 4(1):p. 69-77 (2003); Ank, N., et al., *J. Interferon & Cytokine Res.* 26:373-379 (2006)). In particular, the association of the Arg70 allele with poorer response to IFN-α suggests that the presence of this allele negatively affects an individual's ability to mount essential components of the immune response to HCV that are involved in achieving an SVR to IFN-α based therapy. This may be due to reduced functioning of the Arg70 isoform relative to the Lys70 isoform, to interference of the Arg70 isoform with functioning of the Lys70 isoform, or a combination of both effects. Reduced levels of the Arg70 isoform in the serum is the most likely explanation for the poorer response phenotype given the inventors discovery that a human cell line engineered to express a myc-tagged version of either the Lys70 isoform or the Arg70 isoform secrete significantly larger amounts of the Lys70 isoform.

The SNPs associated with response to IFN-α therapy are described in Table 1 below, which lists the polymorphic site (PS) where the SNP is located, identified with the NCBI SNP Database designation, the alternative alleles that are found at the PS, the allele that is associated with better response to IFN-α therapy, and the heterozygous and homozygous genotypes comprising this allele, which are referred to herein as IFN-α response markers.

TABLE 1

IFN-α Response Markers

| PS | SNP | Better Response Allele | Heterozygous IFN-α Response Marker | Homozygous IFN-α Response Marker |
|---|---|---|---|---|
| rs12979860 | T/C | C | C/T genotype | C/C genotype |
| rs28416813 | G/C | G | G/C genotype | G/G genotype |
| rs8103142 | A/G | A | A/G genotype | A/A genotype |
| rs12980275 | A/G | A | A/G genotype | A/A genotype |
| rs8099917 | A/C | A | A/C genotype | A/A genotype |
| rs12972991 | T/G | T | T/G genotype | T/T genotype |
| rs8109886 | A/C | C | C/A genotype | C/C genotype |
| rs4803223 | T/C | T | T/C genotype | T/T genotype |
| rs12980602 | A/G | A | A/G genotype | A/A genotype |

The inventors herein contemplate that testing individuals for the presence of one or more of the IFN-α Response Markers in Table I will be useful in a variety of pharmacogenetic products and methods that involve identifying individuals most likely to respond to IFN-α therapy for a disease susceptible to treatment with IFN-α, for identifying individuals chronically infected with HCV who may benefit from supplementing combination interferon alpha/ribavirin therapy with a therapy that increases levels of the Lys70 IFN-λ3 isoform, decreases levels of the Arg70 IFN-λ3 iso form or does both, and in helping physicians decide whether to prescribe antiviral therapy to a patient acutely infected with HCV.

Accordingly, in one embodiment, the invention provides a pharmaceutical composition comprising an interferon alpha (IFN-α) for treating an individual having a disease susceptible to treatment with the IFN-α and a positive test for at least one IFN-α response marker.

In another embodiment, the invention provides the use of an IFN-α in the manufacture of a medicament for treating an individual having a disease susceptible to treatment with the IFN-α and a positive test for at least one IFN-α response marker.

In yet another embodiment, the invention provides a drug product which comprises an IFN-α pharmaceutical composition and prescribing information which includes a pharmacogenetic indication for which the pharmaceutical composition is recommended. The pharmacogenetic indication includes two components: a disease susceptible to treatment with the IFN-α in the pharmaceutical composition and patients who have the disease and who are genetically defined by having at least one IFN-α response marker.

The invention also provides a method of testing an individual for the presence or absence of at least one IFN-α response marker, the method comprising obtaining a nucleic acid sample from the individual and assaying the sample to determine the individual's genotype for at least one of the polymorphic sites in Table 1.

In another embodiment, the invention provides a method of testing an individual for the presence or absence of an IFN-α response marker at the rs8103142 PS, the method comprising obtaining a biological sample from the individual and assaying the biological sample for the presence of IFN-λ3 with Lys at amino acid position 70 or for the presence of IFN-λ3 with Arg at amino acid position 70. In some embodiments, the assaying step comprises contacting the biological sample with a monoclonal antibody that is capable of distinguishing between IFN-λ3 with Lys at amino acid position 70 and IFN-λ3 with Arg at amino acid position 70.

In some embodiments, the method of testing individuals for the presence or absence of an IFN-α response marker further comprises generating a test report that indicates the individual's genotype for the assayed polymorphic site and optionally providing the test report to the individual or to a physician who is treating the individual for a disease susceptible to treatment with the IFN-α.

In another aspect, the invention provides a kit for detecting an IFN-α response marker in a nucleic acid sample. The kit comprises a set of one or more oligonucleotides designed for identifying each of the alleles at the polymorphic site in the IFN-α response marker. In some embodiments, the nucleic acid sample is from a patient having a disease susceptible to treatment with an IFN-α. In one embodiment, the disease is a chronic HCV infection, the subject has previously received a liver transplant, and the nucleic acid sample is from a liver biopsy of the transplanted liver. In another embodiment, the nucleic acid sample is from a donor liver that is being tested for transplantation into a patient with a chronic HCV infection.

In a still further embodiment, the invention provides a method of selecting a therapy for treating an individual having a disease susceptible to treatment with an IFN-α, comprising determining whether the individual has at least one IFN-α response marker and selecting a therapy based on the results of the testing step, wherein if the individual has the IFN-α response marker, the selected therapy comprises initial treatment or continued treatment with the IFN-α and if the individual lacks the interferon IFN-α response marker, the selected therapy either comprises administering the IFN-α in combination with at least one other therapeutic agent that is not an IFN-α or excludes IFN-α-based therapy.

The invention also provides a screening method for selecting individuals for initial treatment or continued treatment with an IFN-α from a group of individuals having a disease susceptible to treatment with the IFN-α. This screening method comprises testing each member of the disease group for the presence of at least one IFN-α response marker and selecting for treatment at least one individual testing positive for the FN-α response marker.

In each of the above embodiments, the IFN-α response marker is any of the heterozygous and homozygous IFN-α response markers shown in Table 1. In preferred embodiments, the IFN-α response marker is one of the homozygous response markers. In one preferred embodiment, the IFN-α response marker is an A/A genotype at the rs8103142 PS or a G/G genotype at the rs28416813. In other embodiments, the prediction of response to an IFN-α is based on the presence of an IFN-α response marker for at least two PS in Table 1.

In yet a further embodiment, the invention provides a method of predicting whether a patient having a chronic HCV infection will respond to combination therapy comprising an IFN-α-2 and ribavirin. The method comprises obtaining a nucleic acid sample from the individual, assaying the nucleic acid sample for the presence of at least one homozygous IFN-α response marker of Table 1 and making a prediction based on the results of the assaying step. If the results are positive for the presence of the homozygous IFN-α response marker, the prediction is that the individual is likely to achieve an SVR, and if the results are negative for the presence of the homozygous IFN-α response marker (e.g., the individual has a C/T genotype or a T/T genotype at the rs12979860 polymorphic site), the prediction is that the individual is not likely to achieve a SVR. In one embodiment, the patient has previously received a liver transplant and the nucleic acid sample is from a liver biopsy of the transplanted liver.

In a still further embodiment, the invention provides a method of treating an individual for a chronic HCV infection. The method comprises obtaining the individual's genotype for at least one of the polymorphic sites in Table 1 and prescribing a treatment regimen based on the obtained genotype. If the genotype is one of the homozygous IFN-α response markers, then the treatment regimen comprises administering to the individual an interferon alpha in combination with ribavirin. In some embodiments, the treatment regimen for an individual with a homozygous IFN-α response marker comprises administering to the individual therapeutically effective amounts of a pegylated interferon alpha, ribavirin and at least one other antiviral agent. In some embodiments, the other antiviral agent is an HCV protease inhibitor or an HCV polymerase inhibitor. If the obtained genotype is not a homozygous IFN-α response marker (i.e., is heterozygous or homozygous for the poorer response allele), then in some embodiments the prescribed treatment regimen comprises one or more antiviral agents that is not an interferon alpha, and in some preferred embodiments such antiviral agents are selected from HCV protease inhibitors, HCV polymerase inhibitors, and therapeutics that increase levels of the Lys70 IFN-λ3 isoform, decrease levels of the Arg70 IFN-λ3 isoform or does both.

In yet another embodiment, the invention provides a drug product comprising an IFN-λ3 Lys70 pharmaceutical composition and prescribing information which states the pharmaceutical composition is recommended for treating an individual infected with HCV and a positive test for the presence of a G allele at rs8103142. The IFN-λ3 Lys70 pharmaceutical composition comprises an IFN-λ3 Lys70 polypeptide or an expression vector which encodes an IFN-λ3 Lys70 polypeptide. In preferred embodiments, the prescribing information further states that the IFN-λ3 Lys70 pharmaceutical composition is for use in combination with an IFN-α-based therapy.

In a still further embodiment, the invention provides a pharmaceutical composition that specifically neutralizes the activity of IFN-λ3 Arg 70 but not IFN-λ3 Lys 70. In some embodiments, the pharmaceutical composition comprises a monoclonal antibody which specifically binds to and neutralizes a polypeptide comprising amino acids 23-196 of FIG. 4 (SEQ ID NO:10) in which arginine is substituted for lysine at amino acid position 70, but does not bind to a polypeptide comprising amino acids 23-196 of SEQ ID NO:10 in which lysine is present at amino acid position 70. In other embodiments, the neutralizing pharmaceutical composition comprises a molecule which inhibits expression of IFN-λ3 Arg 70 but not IFN-λ3 Lys 70. In some embodiments, the molecule is an antisense RNA, siRNA or a ribozyme.

In some embodiments of any of the above compositions and methods in which the disease susceptible to treatment with an IFN-α is a chronic HCV infection, the chronic HCV infection is a high baseline viral load infection with an HCV genotype selected from the group consisting of genotype 1 (G1 HCV), genotype 3 (G3 HCV) or genotype 4 (G4 HCV).

In all of the above embodiments, the IFN-α is preferably a pegylated IFN-α-2a or pegylated IFN-α-2b, and in particularly preferred embodiments, the IFN-α is PEGASYS® (peginterferon alfa-2a) or PegIntron® (peginterferon alfa-2b).

In all of the above embodiments, the patient with a disease susceptible to treatment with an IFN-α failed to respond adequately to previous therapy with an IFN-α.

In all of the above embodiments, a positive test for an IFN-α response marker may be used in combination with the presence of one or more other predictors of positive response to IFN-α therapy to identify patients who are likely to respond to initial or continued therapy with an IFN-α.

In a still further embodiment, the invention provides a method for estimating a probability that a patient having a chronic HCV genotype 1 infection will achieve a sustained viral response to combination therapy with a pegylated IFN-α-2 and ribavirin. The method comprises obtaining a set of genetic and clinical response predictors of the patient's response, inputting the obtained predictors into a computer that runs a logistic regression model on the inputted predictors to calculate the estimated probability, and transmitting the estimated probability to the patient or to the patient's physician, wherein the patient is self-identified as African American or Caucasian, wherein the set of genetic and clinical response predictors consists of the patient's genotype at the rs12979860 polymorphic site, the patient's baseline HCV viral load, the patient's self-identified ethnicity and the patient's METAVIR score for baseline fibrosis and wherein the logistic regression model is $$P = \frac{1}{1 + e^{-[(1.4 \times G)+(1.7 \times V)+(1.1 \times E)+(1.1 \times F)-3.8]}},$$

where
P: Probability of achieving SVR;
G: rs12979860 genotype: TT=0, CT=1, CC=2;
V: Baseline viral load: ≧600,000 IU/mL=0, <600,000 IU/mL=1;
E: Ethnicity: African Ancestry=0, Caucasian=1; and
F: Baseline fibrosis: METAVIR F3-4=0, F0-2=1.

In a still further embodiment, the invention provides a method of treating an individual diagnosed with an acute HCV infection. The method comprises obtaining the individual's genotype for the rs12979860 PS and making a treatment decision based on the obtained genotype. If the genotype is homozygous T, then the treatment decision to start the patient on an antiviral therapy. If the genotype is heterozygous C or homozygous C, the treatment decision is to withhold antiviral therapy until the individual is diagnosed with a chronic HCV infection.

BRIEF DESCRIPTION OF THE DRAWINGS

FIG. 4 illustrates a reference amino acid sequence for human precursor interleukin 28B (IFN-lambda 3): the 196 amino acid NCBI Reference Sequence NP_742151.2, GI:28144901 (SEQ ID NO:10), with the predicted signal peptide underlined and the location of variant amino acid positions reported in the NCBI SNP database as of Jun. 15, 2009 indicated by bold letters in the reference sequence and the identity of the variant allele indicated by a bold letter below the variant amino acid position.

FIG. 5 illustrates the reduced secretion of the IFN-λ3 Arg70 isoform relative to the IFN-λ3 Lys70 isoform when expressed as myc-tagged constructs in 293 T cells, with FIG. 5A showing a Comassie Blue-stained gel of total protein present in the supernatant at 48 hours after transfection with the indicated expression construct and FIG. 5 B showing a Western blot of a duplicate gel probed with an anti-myc antibody.

DETAILED DESCRIPTION OF THE INVENTION

I. Definitions

Figure 1:
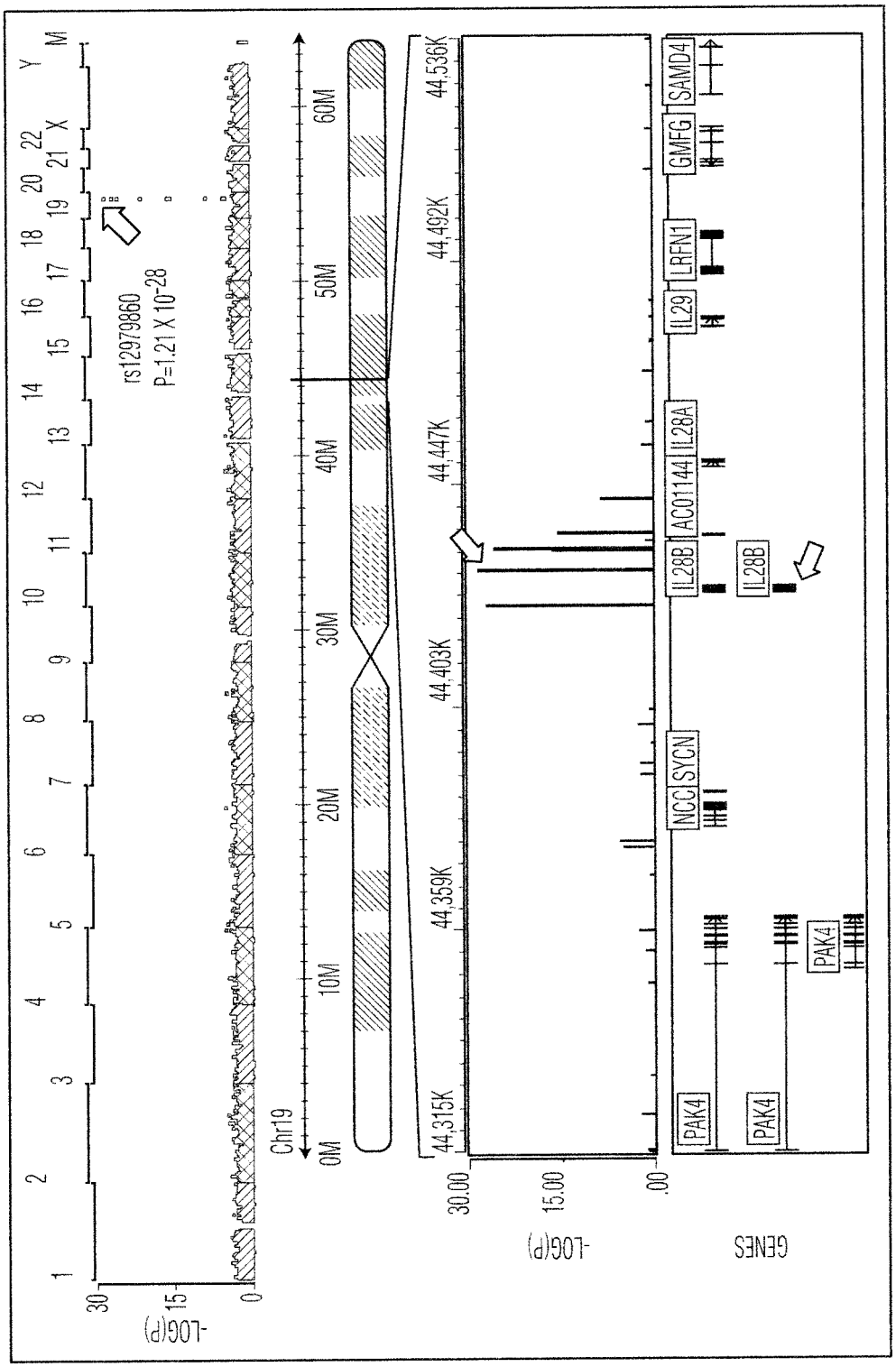
FIG. 1 illustrates the results of single-marker genotype trend tests for significant determinants of sustained viral response (SVR) in a combined group of Caucasian, African American and Hispanic patients chronically infected with HCV genotype 1 and treated with peginterferon alfa-2/ribavirin combination therapy. The top and middle graphs show the p values of all genotyped SNPs (Y-axis) from the genome wide and chromosome 19 analysis, respectively, with red, vertical lines indicating the SNPs that showed genome-wide significant association with SVR, the red arrow indicating the rs12979860 SNP. The bottom graph shows the location of known genes on chromosome 19 identified by vertical bars, with several genes identified by name and the location of the IL-28B gene indicated by the blue arrow. Further details are found in the Examples.

So that the invention may be more readily understood, certain technical and scientific terms are specifically defined below. Unless specifically defined elsewhere in this document, all other technical and scientific terms used herein have the meaning that would be commonly understood by one of ordinary skill in the art to which this invention belongs when used in similar contexts as used herein.

As used herein, including the appended claims, the singular forms of words such as "a," "an," and "the," include their corresponding plural references unless the context clearly dictates otherwise.

"About" when used to modify a numerically defined parameter, e.g., the dosage for a therapeutic agent discussed herein, or the length of treatment time, means that the parameter may vary by as much as 10% above or below the stated numerical value for that parameter. For example, a dosage of about 1.5 µg/kg or PegIntron® (peginterferon alfa-2b) used in the treatment of HCV patients could vary between 1.30 µg/kg and 1.65 µg/kg.

"Allele" is a particular form of a gene or other genetic locus, distinguished from other forms by its particular nucleotide sequence, the term allele also includes one of the alternative polymorphisms (e.g., a SNP) found at a polymorphic site.

"Beneficial result" means a desired clinical result of treatment with an IFN-α, including but not limited to: alleviation of one or more disease symptoms, diminishment of extent of disease (e.g., reduction in viral load), stabilized (i.e., not worsening) state of disease, slowing of disease progression, amelioration or palliation of a disease state, prolonging survival (as compared to expected survival if not treated), relapse-free survival, remission (whether partial or total) and cure (i.e., elimination of the disease).

"Consists essentially of" and variations such as "consist essentially of" or "consisting essentially of" as used throughout the specification and claims, indicate the inclusion of any recited elements or group of elements, and the optional inclusion of other elements, of similar or different nature than the recited elements, which do not materially change the basic or novel properties of the specified dosage regimen, method, or composition.

"Individual" or "animal" or "patient" or "mammal," is meant any subject, particularly a mammalian subject, for whom any of the claimed compositions and methods is needed or may be beneficial. In preferred embodiments, the individual is a human. In more preferred embodiments, the individual is an adult human, i.e., at least 18 years of age.

"IFN-α response" means a desired clinical result of treatment with an IFN-α, including but not limited to: alleviation of one or more disease symptoms, diminishment of extent of disease, stabilized (i.e., not worsening) state of disease, slowing of disease progression, amelioration or palliation of a disease state, prolonging survival (as compared to expected survival if not treated), relapse-free survival, remission (whether partial or total) and cure (i.e., elimination of the disease).

"IFN-α treatment naïve" means that the individual or patient who is to be treated or tested according to any of the embodiments described herein has not been previously treated with any IFN-α, including any experimental or approved IFN-α drug product.

"Interferon-lambda 3" or "IFN-λ3" means a polypeptide comprising amino acids 23-196 of SEQ ID NO:10 (contiguous amino acids in FIG. 4), and includes naturally occurring allelic variants of SEQ ID NO:10, in which the reference amino acid at one or more of the variant positions shown in FIG. 4 is substituted with the variant amino acid. An IFN-λ3 Lys70 polypeptide is an IFN-λ3 isoform having lysine at amino acid position 70 of FIG. 3 and an IFN-λ3 Arg70 polypeptide is an IFN-λ3 isoform having arginine at amino acid position 70 of FIG. 4. In the context of therapeutic compositions and methods described herein, the term "IFN-λ3 Lys70 polypeptide" includes derivatives thereof in which the amino acid backbone is covalently attached to other molecules to provide one or more desirable properties such as longer in vivo half-life or reduced immunogenicity. Nonlimiting examples of IFN-λ3 Lys70 polypeptide derivatives useful in the present invention are glycosylated derivatives, pegylated derivatives, and fusions between the IFN-λ3 Lys70 polypeptide and a non-interferon protein such as human serum albumin or an IgG. In the context of therapeutic compositions and methods described herein, the term "IFN-λ3 Lys70 polypeptide" also includes cysteine mutants in which one or more of the seven cysteine residues of SEQ ID NO:10 is replaced with another amino acid to facilitate recombinant production of an IFN-λ3 Lys70 composition having a single disulfide bonding pattern as described in U.S. Pat. No. 7,517, 961. Preferred cysteine mutants include replacement of the second or third Cys residues of SEQ ID NO:10 with serine, alanine, threonine, valine or asparagine.

"IFN-λ3 Lys70 pharmaceutical composition" means a pharmaceutically acceptable carrier, diluent or excipient and either (1) an IFN-λ3 Lys70 polypeptide or (2) an expression vector which comprises a nucleotide sequence that encodes an IFN-λ3 Lys70 polypeptide operably linked to a promoter sequence that is capable of driving expression of the IFN-λ3 Lys70 polypeptide in at least one human tissue. In preferred embodiments, the human tissue is liver.

"Isolated" is typically used to reflect the purification status of a biological molecule such as RNA, DNA, oligonucleotide, or protein, and in such context means the molecule is substantially free of other biological molecules such as nucleic acids, proteins, lipids, carbohydrates, or other material such as cellular debris and growth media. Generally, the term "isolated" is not intended to refer to a complete absence of other biological molecules or material or to an absence of water, buffers, or salts, unless they are present in amounts that substantially interfere with the methods of the present invention.

"Locus" refers to a location on a chromosome or DNA molecule corresponding to a gene, a physical feature such as a polymorphic site, or a location associated with a phenotypic feature.

"Nucleotide pair" is the set of two nucleotides (which may be the same or different) found at a polymorphic site on the two copies of a chromosome from an individual.

"Oligonucleotide" refers to a nucleic acid that is usually between 5 and 100 contiguous bases in length, and most frequently between 10-50, 10-40, 10-30, 10-25, 10-20, 15-50, 15-40, 15-30, 15-25, 15-20, 20-50, 20-40, 20-30 or 20-25 contiguous bases in length. The sequence of an oligonucleotide can be designed to specifically hybridize to any of the allelic forms of a locus; such oligonucleotides are referred to as allele-specific probes. If the locus is a PS comprising a SNP, the complementary allele for that SNP can occur at any position within an allele-specific probe. Other oligonucleotides useful in practicing the invention specifically hybridize to a target region adjacent to a PS with their 3' terminus located one to less than or equal to about 10 nucleotides from the PS, preferably about 5 nucleotides. Such oligonucleotides hybridizing adjacent to a PS are useful in polymerase-mediated primer extension methods and are referred to herein as "primer-extension oligonucleotides". In a preferred embodiment, the 3-terminus of a primer-extension oligonucleotide is a deoxynucleotide complementary to the nucleotide located immediately adjacent to the PS.

"Parenteral administration" means an intravenous, subcutaneous, or intramuscular injection.

"Pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In another embodiment, this term refers to molecular entities and compositions approved by a regulatory agency of the federal or a state government or listed in the U.S. Pharmacopeia or another generally recognized pharmacopeia for use in animals, and more particularly in humans.

"Polymorphic site" or "PS" refers to the position in a genetic locus or gene at which a polymorphism is found, e.g., single nucleotide polymorphism (SNP), restriction fragment length polymorphism (RFLP), variable number of tandem repeat (VNTR), dinucleotide repeat, trinucleotide repeat, tetranucleotide repeat, simple sequence repeat, insertion element such as Alu, and deletion or insertion of one or more nucleotides). A PS is usually preceded by and followed by highly conserved sequences in the population, of interest and thus the location of a PS is typically made in reference to a consensus nucleic acid sequence of thirty to sixty nucleotides that bracket the PS, which in the case of a SNP is commonly referred to as the "SNP context sequence". The location of the PS may also be identified by its location in a consensus or reference sequence relative to the initiation codon (ATG) for protein translation. The skilled artisan understands that the location of a particular PS may not occur at precisely the same position in a reference or context sequence in each individual in a population of interest due to the presence of one or more insertions or deletions in that individual as compared to the consensus or reference sequence. Moreover, it is routine for the skilled artisan to design robust, specific and accurate assays for detecting the alternative alleles at a polymorphic site in any given individual, when the skilled artisan is provided with the identity of the alternative alleles at the PS to be detected and one or both of a reference sequence or context sequence in which the PS occurs. Thus, the skilled artisan will understand that specifying the location of any PS described herein by reference to a particular position in a reference or context sequence (or with respect to an initiation codon in such a sequence) is merely for convenience and that any specifically enumerated nucleotide position literally includes whatever nucleotide position the same PS is actually located at in the same locus in any individual being tested for the presence or absence of a genetic marker of the invention using any of the genotyping methods described herein or other genotyping methods well-known in the art.

"Treat" or "Treating" means to administer a therapeutic agent, such as a composition containing any of the interferon alpha proteins described herein, internally or externally to an individual in need of the therapeutic agent. Individuals in need of the agent include individuals who have been diagnosed as having, or at risk of developing, a condition or disorder susceptible to treatment with the agent, as well as individuals who have, or are at risk of developing, one or more adverse effects of treatment with a first therapeutic agent that are susceptible to alleviation with a second therapeutic agent. Typically, the therapeutic agent is administered in a therapeutically effective amount, which means an amount effective to produce one or more beneficial results. The therapeutically effective amount of a particular agent may vary according to factors such as the disease state, age, and weight of the patient being treated, and the sensitivity of the patient, e.g., ability to respond, to the therapeutic agent. Whether a beneficial or clinical result has been achieved can be assessed by any clinical measurement typically used by physicians or other skilled healthcare providers to assess the presence, severity or progression status of the targeted disease, symptom or adverse effect. Typically, a therapeutically effective amount of an agent will result in an improvement in the relevant clinical measurement(s) over the baseline status, or over the expected status if not treated, of at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%. While an embodiment of the present invention (e.g., a treatment method or article of manufacture) may not achieve the desired clinical benefit or result in every patient, it should do so in a statistically significant number of patients as determined by any statistical test known in the art such as the Student's t-test, the chi²-test, the U-test according to Maim and Whitney, the Kruskal-Wallis test (H-test), Jonckheere-Terpstra-test and the Wilcoxon-test.

"Viral load" in the context of treating chronic HCV infection means the quantity of HCV RNA in the serum of a patient (also referred to in the art and herein as serum HCV RNA and HCV viral load). The viral load is preferably measured using a quantitative RT-PCR assay, e.g., such as the assay described in the Examples section herein or any other assay that employs different methodology but is generally accepted in the art as providing an equivalent or similar result. More preferably, the RT-PCR assay used to measure an individual's HCV viral load has a lower limit of quantitation (LLQ) of about 29 international units/mL (IU/mL) or less. Quantifying a patient's HCV viral load at baseline and at various time points during treatment with antiviral therapy is useful to classify whether the patient has a high baseline viral load, as defined herein, and to assign the patient to a viral response phenotype, including any one of the viral response phenotypes described herein.

"Baseline viral load" means the serum HCV RNA level prior to initiation of therapy with one or more antiviral agents. A "high baseline viral load" means a quantity of HCV RNA that is generally understood in the art as classifying a patient as having a difficult to treat chronic HCV viral infection. Two baseline viral load values that have been used to classify patients as difficult to treat in the context of indirect peginterferon alfa/ribavirin therapy are >600,000 IU/ml and >800,000 IU/ml. Recently, a viral load used to classify patients as being difficult to treat is >400,000 IU/ml.

"Undetectable HCV RNA" means that HCV RNA was not detected using an RT-PCR assay with a lower limit of detection (LLD) of about 10 IU/ml or less or any other assay that employs different methodology but is generally accepted in the art as providing an equivalent or similar sensitivity.

"Viral response" in the context of treating chronic HCV infection means a reduction in the level of serum HCV RNA after initiation of antiviral therapy.

In some embodiments, the antiviral therapy comprises an interferon alpha. In other embodiments, the therapy comprises an interferon alpha and one or more additional antiviral agents. Combination therapy that includes an interferon alpha is frequently referred to in the art as interferon-alpha based therapy. In other embodiments, the viral response being measured is response to antiviral therapy that does not include an interferon alpha. Preferred viral response phenotypes are rapid viral response (RVR), early viral response (EVR), end of treatment response (ETR), sustained viral response (SVR), slow response, null response, nonresponse (NR) and relapse. The definitions and time points for assessing these response phenotypes are described below. In some embodiments, the HCV treatment comprises a lead-in period of indirect antiviral therapy, such as combination peginterferon alpha/ribavirin therapy, followed by "direct antiviral therapy", which as used herein means that the therapy comprises administration of at least one direct antiviral agent, such as an HCV protease inhibitor, optionally in combination with one or more indirect antiviral agents, such as a pegylated interferon and ribavirin. In such multi-phase treatment regimens, the viral response time points described below do not include the lead-in treatment period; rather they refer to the length of treatment with the direct antiviral therapy.

"Rapid viral response" or "RVR" in the context of indirect antiviral combination therapy, e.g., comprising a pegylated interferon-alpha and ribavirin, means undetectable serum HCV RNA at the end of four weeks of treatment.

"Early viral response" or "EVR" means a reduction in serum HCV RNA of $\geq$2 log at the end of 12 weeks of antiviral therapy, with "complete EVR" meaning undetectable serum HCV RNA at the end of 12 weeks of antiviral therapy.

"End of treatment response or "ETR" means undetectable serum HCV RNA at the conclusion of antiviral therapy, and preferably at the conclusion of any of the treatment regimens described herein or at the conclusion of any treatment regimen recommended in prescribing information approved by a regulatory agency. Non-limiting examples of ETR time points are 12, 16, 24, 36 and 48 weeks.

"Sustained viral response" or "SVR" means the undetectable serum HCV RNA at the conclusion of antiviral therapy and at a maximum of 24 weeks following the end of antiviral therapy. In some embodiments, SVR is measured at 12 weeks following the end of antiviral therapy. SVR is also described by Dr. Steven L. Flamm in the *Journal of the American Medical Association*, Vol. 289, No. 18, pp. 2413 to 2417 (2003).

"Slow response", in the context of pegylated interferon alpha/ribavirin combination therapy means $\geq$2 log reduction of, but still detectable, serum HCV RNA at the end of 12 weeks of antiviral therapy and undetectable serum HCV RNA at the end of 24 weeks of antiviral therapy.

"Null response" means <1 log reduction in serum HCV RNA and/or <2 log reduction in serum HCV RNA at the end of 4 weeks and 12 weeks of antiviral therapy, respectively.

"Nonresponse" or "NR" means the presence of detectable HCV RNA throughout a minimum of 12 weeks of antiviral therapy. The nonresponse phenotype is typically assigned if serum HCV RNA is detectable at the end of 4 weeks and at the end of 12 weeks of antiviral therapy.

"Relapse" means the presence of detectable HCV RNA at any time after an end of treatment response (ETR), including but not limited to at 12 weeks or 24 weeks after the ETR.

II. Utility of IFN-α Response Markers of the Invention

The phenotypic effect of the response markers described herein support the use of these markers in a variety of commercial applications, including but not limited to, clinical trials of investigational or previously approved interferon alpha drugs in patients selected on the basis of the presence or absence of one or more of these markers, pharmaceutical compositions and drug products comprising an interferon alpha for treating patients who have at least one of these response markers, diagnostic methods, and pharmacogenetic treatment methods, which involve tailoring a patient's drug therapy based on whether the patient has one or more of these markers.

The utility of any of the commercial applications claimed herein does not require that the correlation between the presence of a genetic marker of the invention and the occurrence of the desired response to the interferon alpha be observed in 100% of the individuals that receive the interferon alpha; nor does it require a diagnostic method or kit to have a specific degree of specificity or sensitivity in determining the presence or absence of a response marker in every individual, nor does it require that a diagnostic method claimed herein be 100% accurate in predicting for every individual whether the individual is likely to have a beneficial response to an interferon alpha. Thus, the inventors herein intend that the terms "determine", "determining" and "predicting" should not be interpreted as requiring a definite or certain result; instead these terms should be construed as meaning that a claimed method provides an accurate result for the majority of individuals, or that the result or prediction for any given individual is more likely to be correct than incorrect.

Preferably, the accuracy of the result provided by a diagnostic method of the invention is one that a skilled artisan or regulatory authority would consider suitable for the particular application in which the method is used. Similarly, the utility of the claimed drug products and treatment methods does not require that they produce the claimed or desired effect in every individual; all that is required is that a clinical practitioner, when applying his or her professional judgment consistent with all applicable norms, decides that the chance of achieving the claimed effect of treating a given individual according to the claimed method or with the claimed drug product is sufficiently high to warrant prescribing the treatment or drug product.

A. Testing for IFN-α Response Markers of the Invention

The presence or absence of an IFN-α response marker may be detected by any of a variety of genotyping techniques commonly used in the art. Typically, such genotyping techniques employ one or more oligonucleotides that are complementary to a region containing, or adjacent to, the PS of interest. The sequence of an oligonucleotide used for genotyping a particular PS of interest is typically designed based on a context sequence for the PS.

The location, in a particular individual, of any of the polymorphic sites identified in Table 1 is at a position corresponding to the location of the PS of interest in a reference coding or genomic DNA sequence surrounding the PS or interest or in one of the context sequences described in Table 2 below, or their complementary sequences. Longer context sequences useful in designing oligonucleotides to genotype the PS of Table 1 are the context sequences listed in the NCBI SNP Database as of May 19, 2009. Reference coding and amino acid sequences for IFN-λ3 are those shown in GenBank Accession No. AY129149 (Version Y129149.1, GI:25527104) in the NCBI Nucleotide database on May 19, 2009.

TABLE 2

Context sequences for SNPs associated with IFN-α response.

| PS | Short Context Sequence[1] | SEQ ID NO |
|---|---|---|
| rs12979860 | CTGAACCAGGGAGCTCCCCGAAGGCG YGAACCAGGGTTGAATTGCACTCCGC | 1 |
| rs28416813 | CAGAGAGAAAGGGAGCTGAGGGAATG SAGAGGCTGCCCACTGAGGGCAGGGG | 2 |
| rs8103142 | TCCTGGGGAAGAGGCGGGAGCGGCAC YTGCAGTCCTTCAGCAGAAGCGACTC | 3 |
| rs12980275 | CTGAGAGAAGTCAAATTCCTAGAAAC RGACGTGTCTAAATATTTGCCGGGGT | 4 |
| rs8099917 | CTTTTGTTTTCCTTTCTGTGAGCAAT KTCACCCAAATTGGAACCATGCTGTA | 5 |
| rs12972991 | AGAACAAATGCTGTATGATTCCCOCT MCATGAGGTGCTGAGAGAAGTCAAAT | 6 |
| rs8109886 | TATTCATTTTTCCAACAAGCATCCTG MCCCAGGTCGCTCTGTCTGTCTCAAT | 7 |
| rs4803223 | CCTAAATATGATTTCCTAAATCATAC RGACATATTTCCTTGGGAGCTATACA | 8 |

TABLE 2-continued

Context sequences for SNPs associated with IFN-α response.

| PS | Short Context Sequence[1] | SEQ ID NO |
|---|---|---|
| rs12980602 | TCATATAACAATATGAAAGCCAGAGA YAGCTCGTCTGAGACACAGATGAACA | 9 |

[1]Context sequences reported in NCBI SNP Database on May 20, 2009;
Y indicates C or T, S indicates G or C, R indicates G or A, K = G or T, M = A or C.

As recognized by the skilled artisan, nucleic acid samples containing a particular PS may be complementary double stranded molecules and thus reference to a particular site on the sense strand refers as well to the corresponding site on the complementary antisense strand. Similarly, reference to a particular genotype obtained for a PS on both copies of one strand of a chromosome is equivalent to the complementary genotype obtained for the same PS on both copies of the other strand. Thus, an A/A genotype for the rs8103142 PS on the coding strand for the IL28B gene is equivalent to a T/T genotype for that PS on the noncoding strand.

The context sequences recited herein, as well as their complementary sequences, may be used to design probes and primers for genotyping the polymorphic sites of Table 1 in a nucleic acid sample obtained from a human subject of interest using any of a variety of methods well known in the art that permits the determination of whether the individual is heterozygous or homozygous for the better response allele identified in Table 1. Nucleic acid molecules utilized in such methods generally include RNA, genomic DNA, or cDNA derived from RNA.

Typically, genotyping methods involve assaying a nucleic acid sample prepared from a biological sample obtained from the individual to determine the identity of a nucleotide or nucleotide pair present at one or more polymorphic sites of interest. Nucleic acid samples may be prepared from virtually any biological sample. For example, convenient samples include whole blood serum, semen, saliva, tears, fecal matter, urine, sweat, buccal matter, skin and hair. Somatic cells are preferred since they allow the determination of the identity of both alleles present at the PS of interest.

Nucleic acid samples may be prepared for analysis using any technique known to those skilled in the art. Preferably, such techniques result in the isolation of genomic DNA sufficiently pure for determining the genotype for the desired polymorphic site(s) in the nucleic acid molecule. To enhance the sensitivity and specificity of that determination, it is frequently desirable to amplify from the nucleic acid sample a target region containing the PS to be genotyped. Nucleic acid isolation and amplification techniques may be found, for example, in Sambrook, et al., Molecular Cloning: A Laboratory Manual (Cold Spring Harbor Laboratory, New York) (2001).

Any amplification technique known to those of skill in the art may be used in practicing the present invention including, but not limited to, polymerase chain reaction (PCR) techniques. PCR may be carried out using materials and methods known to those of skill in the art (See generally PCR Technology: Princzals and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Matilla et al., *Nucleic Acids Res.* 19: 4967 (1991); Eckert et al., PCR Methods and Applications 1: 17 (1991); PCR (eds. McPherson et al., IRL Press, Oxford); and U.S. Pat. No. 4,683,202. Other suitable amplification methods include the ligase chain reaction (LCR) (see Wu and Wallace, *Genomics* 4: 560 (1989) and Landegren et al., *Science* 241: 1077 (1988)), transcription amplification (Kwoh et al., *Proc. Natl. Acad. Sci. USA* 86: 1173 (1989)), self-sustained sequence replication (Guatelli et al., *Proc. Nat. Acad. Sci. USA,* 87: 1874 (1990)); isothermal methods (Walker et al., *Proc. Natl. Acad. Sci. USA* 89:392-6 (1992)); and nucleic acid-based sequence amplification (NASBA).

The amplified target region is assayed to determine the identity of at least one of the alleles present at a PS in the target region. If both alleles of a locus are represented in the amplified target, it will be readily appreciated by the skilled artisan that only one allele will be detected at a PS in individuals who are homozygous at that PS, while two different alleles will be detected if the individual is heterozygous for that PS.

The identity of the allele may be identified directly, known as positive-type identification, or by inference, referred to as negative-type identification. For example, where a SNP is known to be guanine or cytosine in a reference population, a PS may be positively determined to be either guanine or cytosine for an individual homozygous at that site, or both guanine and cytosine, if the individual is heterozygous at that site. Alternatively, the PS may be negatively determined to be not guanine (and thus cytosine/cytosine) or not cytosine (and thus guanine/guanine).

Identifying the allele or pair of alleles (e.g., the two nucleotides in case of a SNP) at a PS in nucleic acid sample obtained from an individual may be accomplished using any technique known to those of skill in the art. Preferred techniques permit rapid, accurate assaying of multiple PS with a minimum of sample handling. Some examples of suitable techniques include, but are not limited to, direct DNA sequencing of the amplified target region, capillary electrophoresis, hybridization of allele-specific probes, single-strand conformation polymorphism analysis, denaturing gradient gel electrophoresis, temperature gradient electrophoresis, mismatch detection; nucleic acid arrays, primer specific extension, protein detection, and other techniques well known in the art. See, for example, Sambrook, et al., Molecular Cloning: A Laboratory Manual (Cold Spring Harbor Laboratory, New York) (2001); Ausubel, et al., Current Protocols in Molecular Biology (John Wiley and Sons, New York) (1997); Orita et al., *Proc. Nat. Acad. Sci. USA* 86, 2766-2770 (1989); Humphries et al., in MOLECULAR DIAGNOSIS OF GENETIC DISEASES, Elles, ed., pp. 32 1-340, 1996; Wartell et al., *Nucl. Acids Res.* 18:2699-706 (1990); Hsu et al. (1994) *Carcinogenesis* 15:1657-1662; Sheffield et al., *Proc. Natl. Acad. Sci. USA* 86:232-6 (1989); Winter et al., *Proc. Natl. Acad. Sci. USA* 82:7575 (1985); Myers et al. (1985) *Nature* 313:495; Rosenbaum and Reissner (1987) *Biophys Chem.* 265:12753; Modrich, *Ann. Rev. Genet.* 25:229-53 (1991); U.S. Pat. No. 6,300,063; U.S. Pat. No. 5,837,832; U.S. Pat. No. 5,459,039; and HuSNP Mapping Assay, reagent kit and user manual, Affymetrix Part No. 90094 (Affymetrix, Santa Clara, Calif.).

In preferred embodiments, the identity of the allele(s) at a PS is determined using a polymerase-mediated primer extension method. Several such methods have been described in the patent and scientific literature and include the "Genetic Bit Analysis" method (WO 92/15712) and the ligase/polymerase mediated genetic bit analysis (U.S. Pat. No. 5,679, 524. Related methods are disclosed in WO 91/02087, WO 90/09455, WO 95/17676, and U.S. Pat. Nos. 5,302,509 and 5,945,283. Extended primers containing the complement of the polymorphism may be detected by mass spectrometry as described in U.S. Pat. No. 5,605,798.

Another primer extension method employs allele specific PCR (Ruano, G. et al., *Nucl. Acids Res.* 17:8392 (1989); Ruano, G. et al., Nucl. Acids Res. 19:6877-82 (1991); WO 93/22456; Turki et al., *J. Gun. Invest.* 95:1635-41 (1995)). In addition, multiple PSs maybe investigated by simultaneously amplifying multiple regions of the nucleic acid using sets of allele-specific primers as described in WO 89/10414.

Yet another primer extension method for identifying and analyzing polymorphisms utilizes single-base extension (SBE) of a fluorescently-labeled primer coupled with fluorescence resonance energy transfer (FRET) between the label of the added base and the label of the primer. Typically, the method, such as that described by Chen et al., *Proc. Nat. Acad. Sci.* 94:10756-61 (1997) uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide.

A preferred genotyping assay is a TaqMan® SNP Genotyping Assay from Applied Biosystems or an assay having about the same reliability, accuracy and specificity.

In all of the above methods, the accuracy and specificity of an assay designed to detect the identity of the allele(s) at any PS is typically validated by performing the assay on DNA samples in which the identity of the allele(s) at that PS is known. Preferably, a sample representing each possible allele is included in the validation process. For diploid loci such as those on autosomal and X chromosomes, the validation samples will typically include a sample that is homozygous for the major allele at the PS, a sample that is homozygous for the minor allele at the PS, and a sample that is heterozygous at that PS. These validation samples are typically also included as controls when performing the assay on a test sample (i.e., a sample in which the identity of the allele(s) at the PS is unknown). The specificity of an assay may also be confirmed by comparing the assay result for a test sample with the result obtained for the same sample using a different type of assay, such as by determining the sequence of an amplified target region believed to contain the PS of interest and comparing the determined sequence to context sequences accepted in the art, such as the context sequences provided herein.

The length of the context sequence necessary to establish that the correct genomic position is being assayed will vary based on the uniqueness of the sequence in the target region (for example, there may be one or more highly homologous sequences located in other genomic regions). The skilled artisan can readily determine an appropriate length for a context sequence for any PS using known techniques such as blasting the context sequence against publicly available sequence databases. For amplified target regions, which provide a first level of specificity, examining the context sequence of about 30 to 60 bases on each side of the PS in known samples is typically sufficient to ensure that the assay design is specific for the PS of interest. Occasionally, a validated assay may fail to provide an unambiguous result for a test sample. This is usually the result of the sample having DNA of insufficient purity or quantity, and an unambiguous result is usually obtained by repurifying or reisolating the DNA sample or by assaying the sample using a different type of assay.

Further, in performing any of the methods described herein that require determining the presence or absence of a particular IFN-α response marker, such determination may be made by consulting a data repository that contains sufficient information on the patient's genetic composition to determine whether the patient has the marker of interest. Preferably, the data repository lists what IFN-α response marker(s) are present and absent in the individual. The data repository could include the individual's patient records, a medical data card, a file (e.g., a flat ASCII file) accessible by a computer or other electronic or non-electronic media on which appropriate information or genetic data can be stored. As used herein, a medical data card is a portable storage device such as a magnetic data card, a smart card, which has an on-board processing unit and which is sold by vendors such as Siemens of Munich Germany, or a flash-memory card. If the data repository is a file accessible by a computer; such files may be located on various media, including: a server, a client, a hard disk, a CD, a DVD, a personal digital assistant such as a Palm Pilot a tape, a zip disk, the computer's internal ROM (read-only-memory) or the internet or worldwide web. Other media for the storage of files accessible by a computer will be obvious to one skilled in the art.

The invention also contemplates that testing for an IFN-α response marker may be determined by determining whether the individual has an allele, e.g., nucleotide, at a different locus that is in high linkage disequilibrium (LD) with the better response allele for any of the SNPs listed in Table 1. Two particular alleles at different loci on the same chromosome are said to be in LD if the presence of one of the alleles at one locus tends to predict the presence of the other allele at the other locus. Such variants, which are referred to herein as linked variants, or proxy variants, may be any type of variant (e.g., a SNP, insertion or deletion) that is in high LD with the better response allele of interest.

Linked variants are readily identified by determining the degree of linkage disequilibrium (LD) between the better response allele of any of the SNPs in Table 1 and a candidate linked allele at a polymorphic site located in the chromosomal region 19q13.13 or elsewhere on chromosome 19. The candidate linked variant may be an allele of a polymorphism that is currently known. Other candidate linked variants may be readily identified by the skilled artisan using any technique well-known in the art for discovering polymorphisms.

The degree of LD between a better response allele in Table 1 and a candidate linked variant may be determined using any LD measurement known in the art. LD patterns in genomic regions are readily determined empirically in appropriately chosen samples using various techniques known in the art for determining whether any two alleles (e.g., between nucleotides at different PSs) are in linkage disequilibrium (see, e.g., GENETIC DATA ANALYSIS II, Weir, Sineuer Associates, Inc. Publishers, Sunderland, Mass. 1996). The skilled artisan may readily select which method of determining LD will be best suited for a particular population sample size and genomic region. One of the most frequently used measures of linkage disequilibrium is $r^2$, which is calculated using the formula described by Devlin et al. (Genomics, 29(2):311-22 (1995)). $r^2$ is the measure of how well an allele X at a first locus predicts the occurrence of an allele Y at a second locus on the same chromosome. The measure only reaches 1.0 when the prediction is perfect (e.g. X if and only if Y).

Preferably, the locus of the linked variant is in a genomic region of about 100 kilobases, more preferably about 10 kb that spans any of the PS of Table 1. Other linked variants are those in which the LD with the better response allele has a $r^2$ value, as measured in a suitable reference population, of at least 0.75, more preferably at least 0.80, even more preferably at least 0.85 or at least 0.90, yet more preferably at least 0.95, and most preferably 1.0. The reference population used for this $r^2$ measurement may be the general population, a population using the IFN-α, a population diagnosed with a particular condition for which the IFN-α shows efficacy (such as chronic HCV infection) or a population whose members are self-identified as belonging to the same ethnic group, such as Caucasian, African American, Hispanic, Latino, Native American and the like, or any combination of these categories. Preferably the reference population reflects the genetic diversity of the population of patients to be treated with an IFN-α.

In some embodiments, a physician determines whether a patient has an IFN-α response marker described herein by ordering a diagnostic test, which is designed to determine whether the patient has at least one better response allele at one or more of the polymorphic sites in Table 1. Preferably the test determines the identity of both alleles, i.e., the genotype, at this PS. In some embodiments, the testing laboratory will prepare a nucleic acid sample from a biological sample (such as a blood sample or buccal swab) obtained from the patient. In some embodiments, a blood sample from the patient is drawn by the physician or a member of the physician's staff, or by a technician at a diagnostic laboratory. In some embodiments, the patient is provided with a kit for taking a buccal swab from the inside of her cheek, which the patient then gives to the physician's staff member or sends directly to the diagnostic laboratory.

In some embodiments, the testing laboratory does not know the identity of the individual whose sample it is testing; i.e., the sample received by the laboratory is made anonymous in some manner before being sent to the laboratory. For example, the sample may be merely identified by a number or some other code (a "sample ID") and the results of the diagnostic method can be reported to the party ordering the test using the sample ID. In preferred embodiments, the link between the identity of an individual and the individual's sample is known only to the individual or to the individual's physician.

In some embodiments, after the test results have been obtained, the testing laboratory generates a test report which indicates whether the better response allele is present or absent at the genotyped polymorphic site, and preferably indicates whether the patient is heterozygous or homozygous for the better response allele. In some embodiments, the test report is a written document prepared by the testing laboratory and sent to the patient or the patient's physician as a hard copy or via electronic mail. In other embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

In one preferred embodiment, if the patient is homozygous for the better response allele, then the test report further indicates that the patient tested positive for a genetic marker associated with a likely response to treatment with an IFN-α, while if the individual is heterozygous for the better response allele or is homozygous for the other allele, then the test report further indicates that the patient tested negative for a genetic marker associated with a likely response to treatment with an IFN-α. In some embodiments, the test result will include a probability score for achieving a beneficial response to the IFN-α, which is derived from running a model that weights various patient parameters (e.g., age, gender, weight, race, test results for other pharmacogenetic markers for the IFN-α) and disease parameters (e.g., disease severity) that are associated with IFN-α response in the relevant disease population. The weight given to each parameter is based on its contribution relative to the other parameters in explaining the inter-individual variability of response to the IFN-α in the relevant disease population. The doctor may use this response probability score as a guide in selecting a therapy or treatment regimen for the patient. For example, for chronic HCV infection, patient parameters associated with achieving SVR include race and disease parameters include HCV genotype, baseline viral load, and degree of fibrosis.

Typically, the individual would be tested for the presence of an IFN-α response marker prior to initiation of IFN-α therapy, but it is envisioned that such testing could be performed at any time after the individual is administered the first dose of an IFN-α. For example, the treating physician may be concerned that the patient has not responded adequately and desires to test the individual to determine whether continued treatment with the IFN-α is warranted. In some embodiments, a physician may determine whether or not an individual should be tested for an IFN-α response marker. For example, the physician may be considering whether to prescribe for the patient a pharmaceutical product that is indicated for patients who test positive for the IFN-α response marker. In embodiments where the patient has detectable serum HCV RNA and has received a liver transplant, the physician may decide to have a biopsy from the transplanted liver tested for an IFN-α response marker to aid making treatment decisions for the patient.

In deciding how to use the IFN-α response marker test results in treating any individual patient, the physician may also take into account other relevant circumstances, such as the disease or condition to be treated, the age, weight, gender, genetic background and race of the patient, including inputting a combination of these factors and the genetic marker test results into a model that helps guide the physician in choosing a therapy and/or treatment regimen with that therapy.

Detecting the presence or absence of any of the response markers in Table 1 may be performed using a kit that has been specially designed for this purpose. In one embodiment, a kit of the invention comprises a set of oligonucleotides designed for identifying each of the alleles at the PS in at least one marker from Table 1, in preferred embodiments the PS is rs12980275, rs28416813 or rs8103142. In another embodiment, the set of oligonucleotides is designed to identify the alleles at any combination of two or more of the PS in Table 1. In a preferred embodiment, the combination of PS comprises at least the rs28416813 PS and the rs8103142 PS. In another preferred embodiment, combination of PS comprises each of the polymorphic sites in Table 1.

In some embodiments, the oligonucleotides in the kit are either allele-specific probes or allele-specific primers. In other embodiments, the kit comprises primer-extension oligonucleotides. In still further embodiments, the set of oligonucleotides is a combination of allele-specific probes, allele-specific primers and primer-extension oligonucleotides. The kit may comprise oligonucleotides designed for detecting the presence of other genetic markers associated with response to interferon alpha.

Oligonucleotides in kits of the invention must be capable of specifically hybridizing to a target region of a polynucleotide. As used herein, specific hybridization means the oligonucleotide forms an anti-parallel double-stranded structure with the target region under certain hybridizing conditions, while failing to form such a structure with non-target regions when incubated with the polynucleotide under the same hybridizing conditions. In some embodiments, the target region contains the PS of interest, while in other embodiments, the target region is located one to 10 nucleotides adjacent to the PS.

The composition and length of each oligonucleotide in the kit will depend on the nature of the genomic region containing the PS as well as the type of assay to be performed with the oligonucleotide and is readily determined by the skilled artisan.

For example, the polynucleotide to be used in the assay may constitute an amplification product, and thus the required specificity of the oligonucleotide is with respect to hybridization to the target region in the amplification product rather than in genomic or cDNA isolated from the individual. As another example, if the kit is designed to genotype two or more polymorphic sites simultaneously, the melting temperatures for the oligonucleotides for each PS in the kit will typically be within a narrow range, preferably less than about 5° C. and more preferably less than about 2° C.

In some embodiments, each oligonucleotide in the kit is a perfect complement of its target region. An oligonucleotide is said to be a "perfect" or "complete" complement of another nucleic acid molecule if every nucleotide of one of the molecules is complementary to the nucleotide at the corresponding position of the other molecule. While perfectly complementary oligonucleotides are preferred for detecting polymorphisms, departures from complete complementarity are contemplated where such departures do not prevent the molecule from specifically hybridizing to the target region as defined above. For example, an oligonucleotide primer may have a non-complementary fragment at its 5' end, with the remainder of the primer being completely complementary to the target region. Alternatively, non-complementary nucleotides may be interspersed into the probe or primer as long as the resulting probe or primer is still capable of specifically hybridizing to the target region.

In some preferred embodiments, each oligonucleotide in the kit specifically hybridizes to its target region under stringent hybridization conditions. Stringent hybridization conditions are sequence-dependent and vary depending on the circumstances. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. As the target sequences are generally present in excess, at Tm, 50% of the probes are occupied at equilibrium.

Typically, stringent conditions include a salt concentration of at least about 0.01 to 1.0 M sodium ion concentration (or other salts) at pH 7.0 to 8.3 and the temperature is at least about 25° C. for short oligonucleotide probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations. Additional stringent conditions can be found in Molecular Cloning: A Laboratory Manual, Sambrook et al., Cold Spring Harbor Press, Cold Spring Harbor, N.Y. (1989), chapters 7, 9, and 11, and in NUCLEIC ACID HYBRIDIZATION, A PRACTICAL APPROACH, Haymes et al., IRL Press, Washington, D.C., 1985.

One non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Stringency conditions with ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete.

The hybridization temperature for hybrids anticipated to be less than 50 base pairs in length should be 5-10° C. less than the melting temperature ($T_m$) of the hybrid, where Tm is determined according to the following equations. For hybrids less than 18 base pairs in length, $T_m$ (° C.)=2(# of A+T bases)+4(# of G+C bases). For hybrids between 18 and 49 base pairs in length, $T_m$(° C.)=81.5+16.6($\log_{10}$[Na+])+0.41(% G+C)−(600/N), where N is the number of bases in the hybrid, and [Na+] is the concentration of sodium ions in the hybridization buffer ([Na+] for 1×SSC=0.165 M).

The oligonucleotides in kits of the invention may be comprised of any phosphorylation state of ribonucleotides, deoxyribonucleotides, and acyclic nucleotide derivatives, and other functionally equivalent derivatives. Alternatively, the oligonucleotides may have a phosphate-free backbone, which may be comprised of linkages such as carboxymethyl, acetamidate, carbamate, polyamide (peptide nucleic acid (PNA)) and the like (Varma, in MOLECULAR BIOLOGY AND BIOTEChNOLOGY, A COMPREHENSIVE DESK REFERENCE, Meyers, ed., pp. 6 17-20, VCH Publishers, Inc., 1995). The oligonucleotides may be prepared by chemical synthesis using any suitable methodology known in the art, or may be derived from a biological sample, for example, by restriction digestion. The oligonucleotides may contain a detectable label, according to any technique known in the art, including use of radiolabels, fluorescent labels, enzymatic labels, proteins, haptens, antibodies, sequence tags and the like. The oligonucleotides in the kit may be manufactured and marketed as analyte specific reagents (ASRs) or may be constitute components of an approved diagnostic device.

In some embodiments, the set of oligonucleotides in the kit have different labels to allow simultaneous determination of the identity of the alleles at two or more polymorphic sites. The oligonucleotides may also comprise an ordered array of oligonucleotides immobilized on a solid surface such as a microchip, silica beads (such as BeadArray technology from Illumina, San Diego, Calif.), or a glass slide (see, e.g., WO 98/20020 and WO 98/20019). Kits comprising such immobilized oligonucleotides may be designed to perform a variety of polymorphism detection assays, including but not limited to probe hybridization and polymerase extension assays.

Kits of the invention may also contain other reagents such as hybridization buffer (e.g., where the oligonucleotides are to be used as allele-specific probes) or dideoxynucleotide triphosphates (ddNTPs; e.g., where the alleles at the polymorphic sites are to be detected by primer extension). Kits designed for use in polymerase-mediated genotyping assays, may also contain a polymerase and a reaction buffer optimized for the polymerase-mediated assay to be performed.

Kits of the invention may also include reagents to detect when a specific hybridization has occurred or a specific polymerase-mediated extension has occurred. Such detection reagents may include biotin- or fluorescent-tagged oligonucleotides or ddNTPs and/or an enzyme-labeled antibody and one or more substrates that generate a detectable signal when acted on by the enzyme.

It will be understood by the skilled artisan that the set of oligonucleotides and reagents for performing the assay will be provided in separate receptacles placed in the kit container if appropriate to preserve biological or chemical activity and enable proper use in the assay.

In other embodiments, each of the oligonucleotides and all other reagents in the kit have been quality tested for optimal performance in an assay designed to determine the genotype for one or more of the PS in Table 1. In some embodiments, the kit includes an instruction manual that describes how to use the determined genotype to assign, to the tested nucleic acid sample, the presence or absence of a response marker.

In some preferred embodiments, the set of oligonucleotides in the kit are allele-specific oligonucleotides. As used herein, the term allele-specific oligonucleotide (ASO) means an oligonucleotide that is able, under sufficiently stringent conditions, to hybridize specifically to one allele of a PS, at a target region containing the PS while not hybridizing to the same region containing a different allele. As understood by the skilled artisan, allele-specificity will depend upon a variety of readily optimized stringency conditions, including salt and formamide concentrations, as well as temperatures for both the hybridization and washing steps.

Examples of hybridization and washing conditions typically used for ASO probes and primers are found in Kogan et al., "Genetic Prediction of Hemophilia A" in PCR PROTOCOLS, A GUIDE TO METHODS AND APPLICATIONS, Academic Press, 1990, and Ruaflo et al., Proc. Natl. Acad. Sci. USA 87:6296-300 (1990).

Typically, an ASO will be perfectly complementary to one allele while containing a single mismatch for the other allele. In ASO probes, the single mismatch is preferably within a central position of the oligonucleotide probe as it aligns with the polymorphic site in the target region (e.g., approximately the 7th or 8th position in a 15mer, the 8th or 9th position in a 16mer, and the 10th or 11th position in a 20mer). The single mismatch in ASO primers is located at the 3' terminal nucleotide, or preferably at the 3' penultimate nucleotide. ASO probes and primers hybridizing to either the coding or non-coding strand are contemplated by the invention.

In some embodiments, the kit comprises a pair of allele-specific oligonucleotides for each PS to be assayed, with one member of the pair being specific for one allele (e.g., the better response allele) and the other member being specific for the other allele. In such embodiments, the oligonucleotides in the pair may have different lengths or have different detectable labels to allow the user of the kit to determine the genotype for the assayed PS.

In still other preferred embodiments, the oligonucleotides in the kit are primer-extension oligonucleotides. Termination mixes for polymerase-mediated extension from any of these oligonucleotides are chosen to terminate extension of the oligonucleotide at the PS of interest, or one base thereafter, depending on the alternative nucleotides present at the PS.

In one embodiment, the kit comprises a pair of allele specific oligonucleotide probes for genotyping at least one of the polymorphic sites in. Table 1. In one embodiment, one ASO probe in the pair comprises a nucleotide sequence of at least 15 nucleotides that is identical to or perfectly complementary to the better response allele of the context sequence shown in Table 2 and the other ASO probe in the pair comprises a nucleotide sequence of at least 15 nucleotides that is identical to or perfectly complementary to the other allele of the context sequence shown in Table 2. In one preferred embodiment, the kit comprises such ASO probes for genotyping at least one PS selected from the group consisting of rs8103142 and rs8103142. In another preferred embodiment, the kit comprises such ASO probes for genotyping both of these PS. In still another embodiment, the kit comprises such ASO probes for genotyping each of the PS in Table 1.

B. Pharmaceutical Compositions, Drug Products and Treatment Regimens

An individual to be tested in, or treated by, any of the methods and products described herein is a human subject in need of treatment with an interferon alpha. In some embodiments, the individual has been diagnosed with, or exhibits a symptom of, a disease susceptible to treatment with an interferon alpha. In other embodiments, the interferon alpha drug to be used has been approved for use in treating an indication with which the individual has been diagnosed. In yet other embodiments, the interferon alpha drug to be used is not approved for treating the diagnosed disease or exhibited symptom(s), but the prescribing physician believes the drug may be helpful in treating the individual.

The IFN-α used in the pharmaceutical compositions, drug products and methods of the present invention may be any of the multiple subtypes of IFN-α proteins expressed in humans and many other species (Pestka, S. et al., *Immunol. Reviews* 202:8-32 (2004); Diaz, M. O., et al., *J. Interferon Cytokine Res* 16:179-180 (1996). In preferred embodiments, the IFN-α protein is a recombinantly produced protein that consists of, or consists essentially of, the mature amino acid sequence for one of the following human IFN-α subtypes: IFN-α1, IFN-α2, IFN-α4, IFN-α5, IFN-α6, IFN-α7, IFN-α8, IFN-α10, IFN-α13, IFN-α14, IFN-α16, IFN-α17, IFN-α21 (Bekisz, J. et al., *Growth Factors* 22(4):243-351 (2004)), as well as allelic variants for any of these subtypes, e.g., IFN-α2a, IFN-α2b, and IFN-α2c. Human IFN-α subtypes share 75-99% amino acid sequence identity and a mature sequence of 166 a.a. except for IFN-α2, which has 165 a.a. due to a deletion at position 44 (Bekisz, J., et al., supra). Other recombinant IFN-α proteins contemplated for use in the present invention include any consensus IFN-α protein in which the amino acid sequence has been designed by selecting at each position the amino acid that most commonly occurs at that position in the various native IFN-α subtypes.

Particularly preferred IFN-α compositions for use in the drug products and methods of the present invention are interferon alpha-2 products approved by a government regulatory agency, including any of the following: Roferon®-A (Interferon-alfa 2A, recombinant) marketed by Hoffmann La-Roche, Nutley N.J.), and pegylated versions thereof, such as PEGASYS® (peginterferon alfa-2a) marketed by Hoffmann La-Roche, Nutley N.J.); INTRON® A (Interferon alfa-2b, recombinant) marketed by Schering Corporation, Kenilworth, N.J.) and pegylated versions thereof, such as PegIntron® (peginterferon alfa-2b); (INFERGEN® (Interferon alfacon-1), a consensus IFN-α originally developed by Amgen, Thousand Oaks, Calif. and currently marketed by Three Rivers Pharmaceuticals, Warrendale, Pa. Other interferons contemplated for use in the present invention include: fusions between interferon alpha and a non-interferon protein, such as Albuferon® (albinterferon alfa-2b) which is being developed by Human Genome Sciences, Rockville, Md. and Norvartis, Basel, Switzerland; Locteron, an investigational controlled release interferon alpha formulation (Biolex/OctoPlus); and Belerofon®, a single amino acid variant of natural alpha interferon, engineered by Nautilus Biotech. Any of the above-named IFN-α compositions may also be sold under different trade names, such as VIRAFERON-PEG® peginterferon alfa-2b, which is the same composition as PegIntron® peginterferon alfa-2b.

PEGASYS® peginterferon alfa-2a is obtained by covalent binding of one 40 kDa branched PEG-polymer via an amide bond to a lysine side chain of an interferon alpha-2b molecule, see, e.g., Dhalluin, C. et al., *Bioconjugate Chem.* 16:504-517 (2005) and U.S. Pat. No. 7,201,897. The resulting product is a mixture of mainly six monopegylated positional isomers (Dhalluin, C., supra, Foser, S. et al., *J. Prot. Exp. Purif.* 30: 78-87 [2003]). PEGASYS® (peginterferon alfa-2a) and biosimilars thereof are also referred to herein as bPEG40K-interferon alfa-2a.

PegIntron® peginterferon alfa-2b is obtained by covalently reacting recombinant interferon-alfa 2b with a succinimidylcarbonate PEG having an average molecular weight of 12,000 Da (SC-PEG12k) in 100 mM sodium phosphate, pH 6.5 (see, e.g., Grace, M. et al., *J Interferon Cytokine Res.* 21:1103-1115 (2001); Wang, Y. S. et al., *Adv. Drug Delivery Rev.* 54:547-570 (2000); and U.S. Pat. No. 5,951,974). The resulting product is a mixture of mainly monopegylated species in which the PEG12k is attached to different residues of interferon alfa-2b via a urethane bond, with the majority positional isomer having the urethane bond at Histidine 34 (see, e.g., Wang, Y. S. et al., supra and U.S. Pat. No. 5,951,974). PegIntron® peginterferon alfa-2b and biosimilars thereof are also referred to herein as PEG12k-interferon alfa-2b.

Other IFN-α products contemplated for use in the invention that have been approved previously or are currently marketed, include: Berofor® alpha 2 (recombinant interferon alpha-2C, Boehringer Ingelheim Pharmaceutical, Inc., Ridgefield, Conn.; interferon alpha-n1, a purified blend of natural alpha interferons known as Sumiferon® (Sumitomo, Japan) or as Wellferon® interferon alpha-n1 (INS), Glaxo-Wellcome Ltd., London, Great Britain; a consensus alpha interferon such as those described in U.S. Pat. Nos. 4,897,471 and 4,695,623 (especially Examples 7, 8 or 9 thereof); ALFERON N Injection® [Interferon alfa-n3 (human leukocyte derived), a mixture of multiple species of natural alpha interferons available from Hemispherx Biopharma, Inc., Philadelphia, Pa.

Other interferon alpha-polymer conjugates useful in the present invention are described in U.S. Pat. No. 4,766,106, U.S. Pat. No. 4,917,888, European Patent Application No. 0 236 987, European Patent Application Nos. 0 510 356, 0 593 868 and 0 809 996 and International Publication No. WO 95/13090.

Also contemplated for use in the present invention is any pegylated interferon alpha 2a or 2b pharmaceutical composition that is approved by a regulatory agency based, at least in part, by reliance on the preclinical and/or clinical data previously submitted to the regulatory authority in connection with approval of any of the above-described marketed pegylated interferon alpha products, i.e., PEGASYS® (peginterferon alfa-2a) and PegIntron® (peginterferon alfa-2b). Such later approved products may be described by the regulatory agency in terms such as a generic of, bioequivalent to, a biosimilar of, or a substitute for the previously approved product, which terms may or may not be explicitly defined by the regulatory agency.

Pharmaceutical compositions of pegylated interferon alphas intended for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose, trehalose), carriers (e.g. human serum albumin), toxicity agents (e.g. NaCl), preservatives (e.g. thimerosol, cresol or benylalcohol), and surfactants (e.g. tween or polysorbates) in sterile water for injection. See, e.g., U.S. Pat. No. 6,180,096 and international Patent Application WO2006/020720. Such compositions may be stored as lyophilized powders under refrigeration at 2°-8° C. and reconstituted with sterile water prior to use. Such reconstituted aqueous solutions are typically stable when stored between and used within 24 hours of reconstitution. See, for example, U.S. Pat. Nos. 4,492,537; 5,762,923 and 5,766,582. Lyophilized pegylated interferon formulations may be provided in a pen-type syringe system that comprises a glass cartridge containing a diluent (i.e., sterile water) in one compartment and the lyophilized pegylated interferon-alpha powder in a separate compartment.

Examples of aqueous pegylated interferon formulations are described in U.S. Pat. No. 5,762,923. Such formulations may be stored in prefilled, multi-dose syringes such as those useful for delivery of drugs such as insulin. Typical suitable syringes include systems comprising a pre-filled vial attached to a pen-type syringe such as the NOVOLET Novo Pen available from Novo Nordisk, as well as prefilled, pen-type syringes which allow easy self-injection by the user.

The present invention also contemplates the use of any of the above Interferon alphas in combination with atoll like receptor (TLR) agonist, which are proposed to induce interferon response. For example, agonists for TLR3, TLR7 and TLR9 are being evaluated for use in treating HCV.

Diseases and conditions that may be treated in accordance with the present invention are generally those that are susceptible to treatment with an IFN-α, i.e., the IFN-α achieves a clinically measurable beneficial result in a group of patients with the disease, e.g., reduction in viral load in HCV-infected patients. Exemplary diseases and conditions susceptible to treatment with an IFN-α include but are not limited to diseases caused by cell proliferation disorders, in particular viral infections, and cancers. Preferably, the disease is one for which the IFN-α has been approved by a regulatory agency such as the U.S. Food and Drug Administration.

Viral infections include hepatitis A, hepatitis B, hepatitis C, hepatitis D, other non-A/non-B hepatitis, herpes virus, Epstein-Barr virus (EBV), cytomegalovirus (CMV), herpes simplex, human herpes virus type 6, papilloma, poxvirus, picornavirus, adenovirus, rhinovirus, human T lymphotropic virus-type 1 and 2, human rotavirus, rabies, retroviruses including human immunodeficiency virus (HIV), encephalitis and respiratory viral infections. In preferred embodiments, the viral infection is HCV or HBV. In a particularly preferred embodiment, the viral infection is chronic HCV infection.

In preferred embodiments, the IFN-α response markers of the present invention are used in conjunction with any IFN-α monotherapy or combination therapy treatment regimen approved by a regulatory authority for a chronic HBV or chronic HCV indication, and in particularly preferred embodiments, in conjunction with any of the dosing and treatment regimens for chronic hepatitis C described in the Package Inserts for the Roferon®-A (Interferon-alfa 2A, recombinant), PEGASYS® (peginterferon alfa-2a), INTRON® A (Interferon alfa-2b, recombinant) and PegIntron® (peginterferon alfa-2b) products. Approved combination therapy regimens for chronic HCV infection typically administer ribavirin, a nucleoside analog, in addition to the IFN-α protein. For the PegIntron® (peginterferon alfa-2b) product, such approved combination regimens recommend therapy for 24 weeks for patients chronically infected with HCV genotype 2 or 3, and up to 48 weeks for patients chronically infected with HCV genotype 1, with 24 weeks therapy approved in Europe for the subset of patients with genotype 1 infection and low viral load (<600,000) patients who are HCV-RNA negative at treatment week four and remain HCV-RNA negative at treatment week 24.

In other embodiments, IFN-α response markers are used in conjunction with viral response testing to determine the appropriate duration of treatment with combination interferon alpha/ribavirin therapy for patients infected with HCV genotype 1. Patients who test positive for a homozygous IFN-α response marker and who have undetectable HCV-RNA at each of treatment weeks 4 and 12 would be candidates for treatment durations of between 12-36 weeks, e.g., 12, 18, 24, 30 or 36 weeks. In some preferred embodiments, the selected treatment duration is 24 weeks for a treatment-naïve patient chronically infected with high baseline viral load, genotype 1 HCV who tests positive for a homozygous IFN-α response marker and has undetectable HCV-RNA at each of treatment weeks 4 and 12. In particularly preferred embodiments, the interferon alpha is a pegylated interferon alpha-2a or 2-b or an albumin-interferon alpha-2a or -2b fusion protein.

IFN-α-based combination regimens comprising a nucleoside analog other than ribavirin are also contemplated for treating. HCV infection in individuals who test positive for an IFN-α response marker. Examples of such nucleoside analogs include ribavirin derivatives such as taribavirin (also known as viramidine and ICN 3142), which is being developed by Valeant Pharmaceuticals International (Aliso Viejo, Calif.) and the compounds described in U.S. Pat. Nos. 6,403, 564 and 6,924,270.

The IFN-α response markers of the present invention may also be used to select patients chronically infected with HCV who are likely to benefit the most from treatment with IFN-α-based therapy (with or without ribavirin) in combination with one or more additional antiviral agents. Non-limiting examples of antiviral agents useful in such combination treatment regimens include an HCV protease inhibitor, an NS3 protease inhibitor, an HCV polymerase inhibitor, an HCV NS5A inhibitor, an IRES inhibitor, an NS4B inhibitor, an HCV helicase inhibitor, an HCV entry inhibitor, an HCV virion production inhibitor, and other interferons.

In one embodiment, the antiviral agent is an HCV protease inhibitor.

HCV protease inhibitors useful in such combination regimens are described in published international application nos. WO2009/038663, WO 2007/092616, and WO 2002/18369 and in published U.S. Patent Application 2007/0042968.

Other HCV protease inhibitors useful in the methods and combination therapies of the present invention include boceprevir (SCHSO3034) and SCH 900518 (Schering-Plough); telaprevir (VX-950), VX-500 and VX-813 (Vertex Pharmaceuticals); MK-7009 (Merck); and ITMN-191 (R7227) (Intennune and Roche); TMC-435 (Medivir/Tibotec); MK-7009 (Merck); GS-9132 and ACH-1095 (Gilead/Achillon);

PHX1766 (Phenomix); ABT-450 HCV (Abbott/Enanta Pharmaceuticals); and BILN 2061 and BI 201335 (Boehringer Ingelheim).

Additional examples of HCV protease inhibitors useful in the methods and combination therapies of the present invention include those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., Biochemistry, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

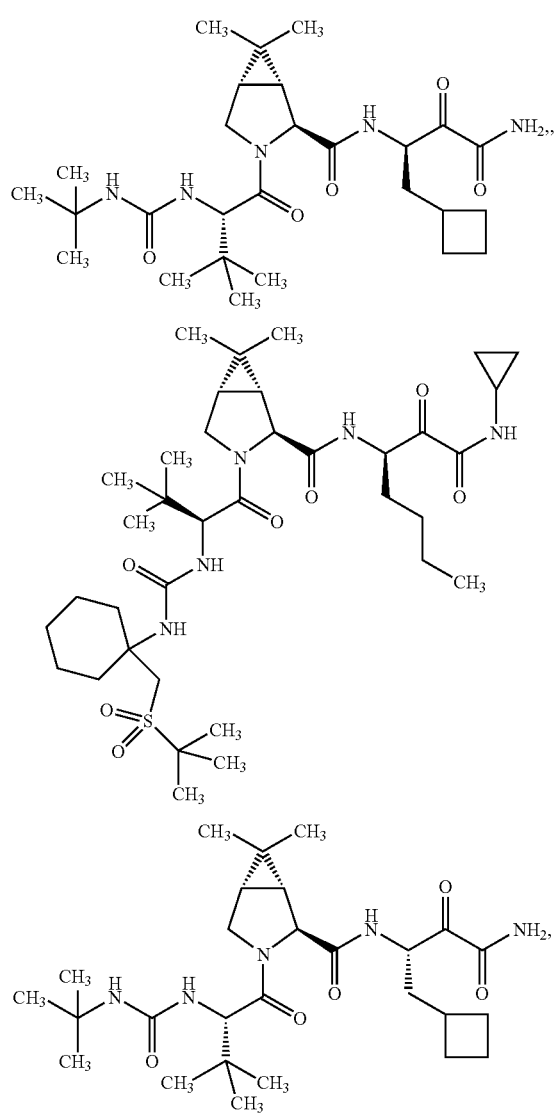

-continued

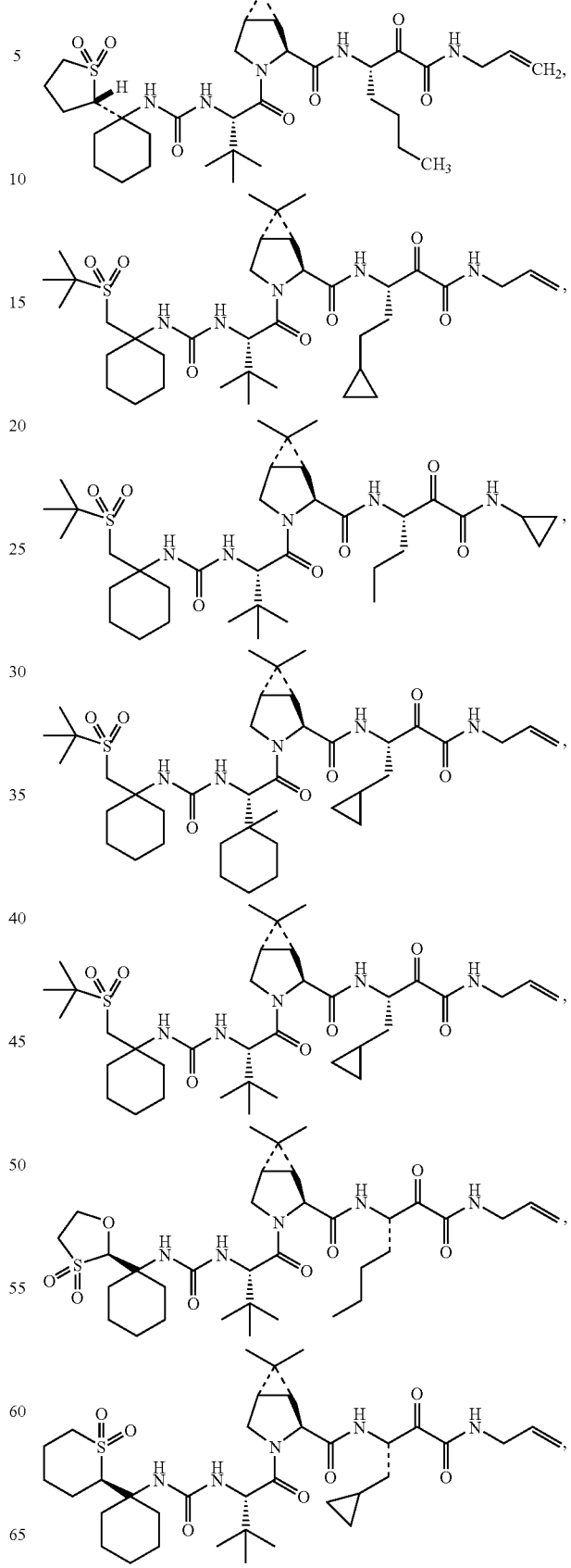

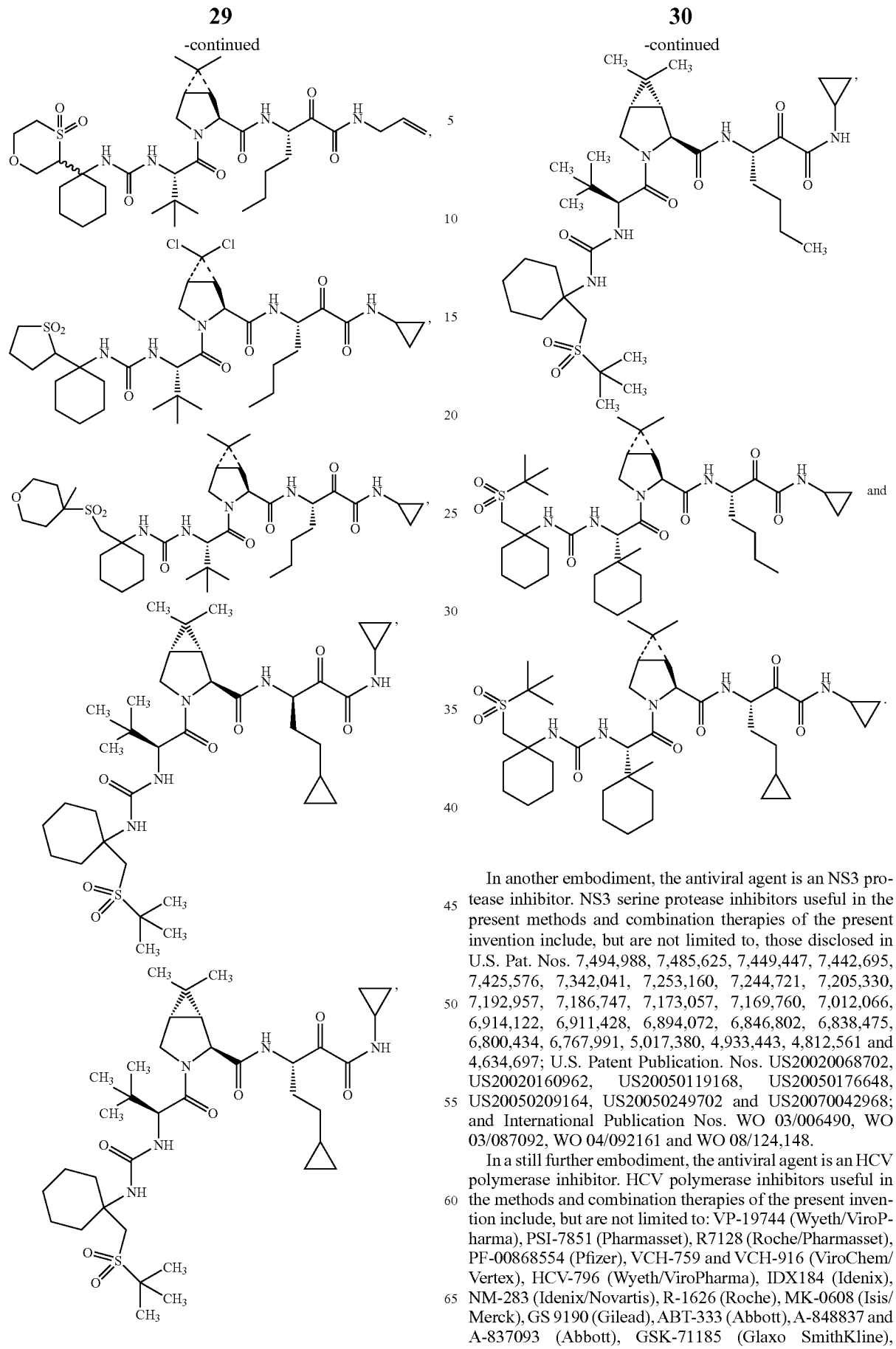

In another embodiment, the antiviral agent is an NS3 protease inhibitor. NS3 serine protease inhibitors useful in the present methods and combination therapies of the present invention include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication. Nos. US20020068702, US20020160962, US20050119168, US20050176648, US20050209164, US20050249702 and US20070042968; and International Publication Nos. WO 03/006490, WO 03/087092, WO 04/092161 and WO 08/124,148.

In a still further embodiment, the antiviral agent is an HCV polymerase inhibitor. HCV polymerase inhibitors useful in the methods and combination therapies of the present invention include, but are not limited to: VP-19744 (Wyeth/ViroPharma), PSI-7851 (Pharmasset), R7128 (Roche/Pharmasset), PF-00868554 (Pfizer), VCH-759 and VCH-916 (ViroChem/Vertex), HCV-796 (Wyeth/ViroPharma), IDX184 (Idenix), NM-283 (Idenix/Novartis), R-1626 (Roche), MK-0608 (Isis/Merck), GS 9190 (Gilead), ABT-333 (Abbott), A-848837 and A-837093 (Abbott), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004), and International Publication Nos. WO 08/082,484, WO 08/082,488, WO 08/083,351, WO 08/136,815, WO 09/032,116, WO 09/032,123, WO 09/032,124 and WO 09/032,125.

In another embodiment, the antiviral agent is an HCV NS5A inhibitor. Nonlimiting examples of HCV NS5A inhibitors useful in the methods and combination therapies of the present invention are AZD2836 (A-831) and AZD7295 (A-689) (Arrow Therapeutics); and BMS-790052 (Bristol-Myers Squibb).

In one embodiment the antiviral agent is an NS4B inhibitor, such as clemizole hydrochloride and other salts of clemizole.

In one embodiment, the antiviral agent is a HCV replicase inhibitor including those disclosed in U.S. Patent Publication No. US20090081636.

In another embodiment, the antiviral agent is an HCV helicase inhibitor such as trioxsalen.

In another embodiment, the antiviral agent is an HCV entry inhibitor, including but not limited to ITX5061 and ITX4520 (iTherx)), PRO 206 (Progenies) and celgosivir (MX-3253), MIGENIX.

In another embodiment the antiviral agent is an RNAi compound, e.g., TT-033 (Tacere Therapeutics, Inc., San Jose, Calif.).

In a still further embodiment, the antiviral agent is another Type I interferon (e.g., IFN-beta or IFN-omega), a Type II interferon (e.g., IFN-gamma or a Type III interferon (e.g., Il-28 or Il-29).

Examples of Type III interferons contemplated for use in the methods and combination therapies of the present invention include, but are not limited to PEG-IFN lambda (Zymo-Genetics/Brisol Myers Squibb).

Examples of further additional antiviral agents contemplated for use in the methods and combination therapies of the present invention include, but are not limited to, TT033 (Benitec/Tacere Bio/Pfizer), Sirna-034 (Sirna Therapeutics), GNI-104 (GENimmune), IDX-102 (Idenix), Levovirin™ (ICN Pharmaceuticals, Costa Mesa, Calif.); Humax (Genmab), ITX-2155 (Ithrex/Novartis), PRO 206 (Progenies), HepaCide-I (NanoVirocides), MX3235 (Migenix), SCV-07 (SciClone Pharma), KPE02003002 (Kemin Pharma), Lenocta (VioQuest Phamiaceuticals), IET—Interferon Enhancing Therapy (Transition Therapeutics), Zadaxin (SciClone Pharma), VP 50406™ (Viropharma, Incorporated, Exton, Pa.); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., N.C.); Alinia (Romark Laboratories), INFORM-1 (a combination of 87128, ITMN-191 and ribavirin); and mycophenolate mofetil (Hoffman-LaRoche, Nutley, N.J.), SCY-635 (SCYNEXIS), ANA773 (Anadys), CYT107 (Cytheris), SPC3649 (Santaris Pharma), Alinia (nitrazoxanide) (Romark); Ogiufanide disodium (Implicit Bioscience), CTS-1027 (Conatus) NOV-205 (Novelos Therapeutics), IMO-2125 (Idera Pharmaceuticals) and CF102 (CAN-FITE).

The invention also contemplates treating HCV patients who are heterozygous or homozygous for the G allele at rs8103142 with a therapeutic agent that increases levels of the Lys70 IFN-λ3 isoform, decreases levels of the Arg70 IFN-λ3 isoform or does both.

Illustrative examples of therapeutic agents that would increase the level of the Lys70 IFN-λ3 isoform include an IFN-λ3 Lys70 polypeptide and an expression vector which encodes an IFN-λ3 Lys70 polypeptide. The IFN-λ3 Lys70 polypeptide may be produced using techniques well known in the art, see, e.g., Dellgren, c. et al., *Genes and Immunity* 10:125-131 (2009) and U.S. Pat. No. 7,517,961. Preferably, the expression vector is one that targets expression of the encoded IFN-λ3 Lys70 polypeptide in human liver hepatocytes. Such liver-targeted gene therapy using adeno-associated viral vectors has been described, see, e.g., Hasbrouck, N.C. et al, Gene Therapy 15:870-875 (2008) and references cited therein, Nancy Smyth Templeton, *Gene and Cell Therapy: Therapeutic Mechanisms and Strategies*, $3^{rd}$ Edition, Published by CRC Press (2008), Mark A. Findeis, *Nonviral vectors for gene therapy: methods and protocols*, Published by Humana Press (2001).

Agents that would decrease the level of the Arg70 IFN-λ3 isoform include antisense RNAs, small interferon RNAs (siRNAS) and ribozymes. The skilled artisan can readily design and test such agents using techniques known in the art. See, e.g., Stanley T. Crooke, *Antisense drug technology: principles, strategies, and applications*, $2^{nd}$ Edition: 2, Published by CRC Press (2007) Kevin J. Scanlon, *Therapeutic applications of ribozymes*, Published by Humana Press (1998).

Another agent that would decrease the level of the Arg70 IFN-λ3 isoform is a monoclonal antibody that binds to and neutralizes the Arg70 iso form, but not the Lys70 isoform. The isolation of such antibodies should be readily achieved since amino acid position 70 is believed to be present on an exterior surface of IFN-λ3.

The rs12979860 C allele is also associated with a greater likelihood of natural clearance of HCV in patients with acute hepatitis C, which refers to the first 6 months after infection with HCV. Between 60% to 70% of infected people develop no symptoms during the acute phase. However, some patients have symptoms of acute hepatitis C infection, which include decreased appetite, fatigue, abdominal pain, jaundice, itching and flu-like symptoms, which lead to an early diagnosis. Other patients are diagnosed with acute hepatitis C due to monitoring for HCV infection after a known exposure to an infected source, such as a needlestick injury. The hepatitis C virus is usually detectable in the blood by PCR within one to three weeks after infection, and antibodies to the virus are generally detectable within 3 to 15 weeks.

Because up to 50% of patients may spontaneously clear the virus from their bodies during the acute phase, physicians have traditionally been reluctant to subject a patient diagnosed with acute hepatitis to the expense and side effects of antiviral therapy unless and until the patient progresses to a chronic HCV infection, i.e., an infection lasting more than 6 months. Determining the patient's genotype at the rs12979860 PS may be another factor the physician could consider in deciding whether to begin antiviral therapy or delay therapy for six months after diagnosis with acute HCV infection. If the patient's genotype is heterozygous or homozygous C, the physician may decide to delay therapy for six months. If the patient's genotype is homozygous T, the physician may decide that early antiviral therapy is warranted since the patient is less likely to spontaneously clear the virus.

The doses and dosage regimen of the other agents used in the combination therapies of the present invention for the treatment of an HCV infection can be determined by the attending clinician, taking into consideration the approved doses and dosage regimen in the package insert; and the age, sex and general health of the patient. Agents administered in HCV combination therapy can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g., one is a tablet and one is a capsule. A kit comprising the separate dosage forms is therefore advantageous.

When the IFN-α is a PEG12k-interferon alfa-2b such as PegIntron® (peginterferon alfa-2b) or a biosimilar thereof, a preferred treatment regimen for chronic HCV infection comprises 1.5 mcg/kg of the PEG12k-interferon alfa-2b once a week in combination with daily doses of 800-1400 mg ribavirin. The ribavirin dose is based on patient weight: 800 mg/day for patients weighing 40-65 kg, 1000 mg/day for patients weighing more than 65 and up to 85 kg, 1200 mg/day for patients weighing more than 85 and up to 105 kg, and 1400 mg/day for patients weighing more than 105 kg. In some embodiments, the recommended weekly dose of the PEG12k-interferon alfa-2b is 0.5, 0.75 or 1.0 mcg/kg and the daily ribavirin dose is between 600-1400 mg ribavirin, based on patient weight.

When IFN-α is a bPEG40K-interferon alfa-2a such as PEGASYS® (peginterferon alfa-2a) or a biosimilar thereof, a preferred treatment regimen for chronic HCV infection comprises 180 mcg/week of the bPEG40K-interferon alfa-2a in combination with a daily ribavirin dose of 1000 mg for patients weighing <75 kg and 1200 mg for patients weighing ≧75 kg. In some embodiments, the recommended weekly dose of the bPEG40K-interferon alfa-2a is at least 25% less than 180 mcg.

In some preferred embodiments, the combination drug regimen used for treating patients chronically infected with high viral load HCV genotype 1 and testing positive for at least one IFN-α, response marker comprises a lead-in treatment period of about 2 to 17 weeks, in which an interferon alpha such as a PEG12k-interferon alfa-2l) and a bPEG40K-interferon alfa-2a is administered in combination with ribavirin, followed by a second treatment period of about 12 to about 28 weeks in which a triple combination of the interferon alpha, ribavirin and a protease inhibitor such as boceprevir or telaprevir is administered. Such two phase treatment regimens are described in the international patent application publication WO 2009/038663. In particularly preferred embodiments, the lead-in period is about 4 weeks and the second treatment period is about 24 weeks.

Cancers susceptible to treatment with an IFN-α include melanoma, chronic myelogenous leukemia (CML), renal cell cancer (RCC), hairy cell leukemia, Kaposi's sarcoma, multiple myeloma, basal cell carcinoma, malignant melanoma, superficial bladder cancer (SBC), ovarian cancer, follicular lymphoma, non-Hodgkin's lymphoma, cutaneous T cell lymphoma, condyloma accuminata, mycosis fungoides, carcinoid syndrome, colorectal cancer, laryngeal papillomatosis, and actinic keratosis. Preferred cancers and dosing regimens therefore are described in the regimens for chronic hepatitis C described in the labeling and prescribing information for the Roferon®-A (Interferon-alfa 2A, recombinant) and INTRON® A (Interferon alfa-2b, recombinant) products.

In preferred embodiments, the IFN-α response markers of the present invention are used in conjunction with a pegylated IFN-α for treating patients with melanoma, chronic myelogenous leukemia (CML) or renal cell cancer (RCC), including, e.g., the treatment regimens described in U.S. Pat. Nos. 6,923, 966 (melanoma), 6,605,273 (RCC) and 6,362,162 (CML); Bukowski R., et al., *Cancer* 95(2):389-396 (2002); Bukowski R., et al., J. Clin Oncol. 20(18):3841-348 (2002); Garcia-Manero, G. et al., *Cancer* 97(12):2010-2016 (2003); Garcia-Manero, G. et al., *Cancer* 98(3): 437-457 (2003); Michallet, M. et al., *Leukemia* 18:309-315 (2004); Motzer, R. J. et al., *J. Clin Oncol.* 19(5):1312-1319 (2001); Motzer, R. J. et al., *Ann. Oncol.* 13:1799-1805 (2002); Lipton, J. H., et al., *Blood* 100: 782a Abstract 3091 (2002); Hochhaus, A., et al., *Blood* 100: 164a Abstract 616 (2002); and Dummer et al., Proc. Am. Soc. Clin. Oncol. 22:712 Abstract 2861 (2003).

In one preferred embodiment, the IFN-α response markers of the invention are used to identify patients with high-risk melanoma who are good candidates for IFN-α therapy, especially patients with Stage IIB (lesions>4 mm, but without positive nodes) and Stage III (lesions>4 mm and node-positive) primary cutaneous melanoma. Preferably the IFN-α therapy is used as adjuvant therapy after the patients have had surgery for their Stage IIB or Stage III melanoma.

In more preferred embodiments, the IFN-α used as adjuvant therapy is a pegylated IFN-α. The melanoma patients treatable in accordance with the improved methods of the present invention include those newly diagnosed with this disease who were free of disease post surgery but at high risk for systemic recurrence of the disease. The term "high risk patients" as used herein means those melanoma patients with lesions of Breslow thickness >4 mm as well as those patients with lesions of any Breslow thickness with primary or recurrent nodal involvement. Treatment with a pegylated IFN-α in accordance with the present invention will continue for up to five years, unless there is clinical evidence of disease progression, unacceptable toxicity or the patient requests that the therapy be discontinued.

When the pegylated IFN-α used for treating a high-risk melanoma patient is a PEG12k-interferon alfa-2b such as PegIntron® (peginterferon alfa-2b) or a biosimilar thereof, a preferred treatment regimen comprises administering to the patient a starting dose of 3.0 to 9.0 micrograms per kilogram once a week (QW), preferably in the range of 4.5 to 6.5 micrograms per kilogram QW, more preferably in the range of 5.5 to 6.5 micrograms per kilogram QW, and most preferably about 6.0 micrograms per kilogram QW. In some preferred embodiments, the high-risk melanoma patient is treated initially with 6.0 micrograms per kilogram of the PEG12k-interferon alfa-2b QW for eight weeks, and then with 3.0 micrograms per kilogram or less of the PEG 12k-interferon alfa-2b QW for a period of five years minus the eight weeks of initial treatment. If less than 3.0 micrograms per kilogram are dosed to the patient, e.g., to maintain patient tolerance to the treatment, the dose is preferably reduced by 1 microgram per kilogram for each reduction, e.g., 3.0 to 2.0 to 1.0.

When the pegylated IFN-α used for treating a high-risk melanoma patient is a bPEG40K-interferon alfa-2a such as PEGASYS® (peginterferon alfa-2a) or a biosimilar thereof, the treatment regimen comprises administering to the patient a dose of about 50 micrograms to about 500 micrograms QW, preferably about 200 micrograms to about 250 micrograms QW.

When administering a combination therapy that is selected to treat a patient based on the presence or absence of an IFN-α response marker in the patient, the therapeutic agents in the combination, or a pharmaceutical composition or compositions comprising the therapeutic agents, may be administered in any order such as, for example, sequentially, concurrently, together, simultaneously and the like. The amounts of the various therapeutic agents in such combination therapy may be different amounts (different dosage amounts) or same amounts (same dosage amounts). In some embodiments, the agents in the combination are administered in doses commonly employed when such agents are used as monotherapy for treating the patient's disease or condition, while in other embodiments, the agents are administered in doses lower than the doses commonly employed when such agents are used as monotherapy for treating the disease or condition.

In some embodiments, the therapeutic agents used in combination therapy are present in the same pharmaceutical composition, which may be suitable for oral administration, intravenous administration, subcutaneous administration or parenteral administration.

The inventors herein also contemplate that the IFN-α response markers described herein could be used to seek regulatory approval to market a new interferon alpha drug product for a pharmacogenetic indication, i.e., an indication that includes a disease component and an IFN-α response marker component. The disease component is a disease susceptible to treatment with the IFN-α and the genetic marker component is a patient who tests positive for at least one of the IFN-α response markers described herein. Similarly, the inventors herein contemplate that these IFN-α response markers are useful for seeking approval of such pharmacogenetic indications for currently approved IFN-α drugs that physicians are reluctant to prescribe for certain diseases based on the marginal benefit/risk ratio of the drug for such diseases in the general population.

Seeking approval for a pharmacogenetic indication typically involves measuring the incidence of a desired response to a drug in two separate groups of patients treated with the drug. Each individual within one of the groups has disease and genetic profiles that place the individual within the proposed pharmacogenetic indication. The individuals in the other group may be randomly selected without regard to whether they have the genetic marker component of the proposed pharmacogenetic indication. Alternately, the individuals are assigned to the other group in a manner that results in a "control" group in which the percentage of individuals who meet and do not meet the genetic marker component is similar to what is observed in the general population, or in a population of patients with the disease component of the proposed pharmacogenetic indication. The drug product for which approval is sought could be administered to the two groups in a prospective trial. Alternatively, a retrospective pharmacogenetic analysis of patients previously treated with the drug could be performed.

The drug product for which a pharmacogenetic indication is being sought could be evaluated with other therapeutically active agents, for example another drug with efficacy for treating the disease or condition in the proposed pharmacogenetic indication or an agent that is intended to reduce the incidence of a an adverse effect caused by the drug. In some embodiments, the pharmacogenetic indication for which regulatory approval is sought may include other markers (genetic markers or biomarkers) or predictors of response to the drug. For example, rapid HCV viral response (RVR) to combination therapy with pegylated interferon alpha and ribavirin is a good predictor of achieving SVR.

The pharmacogenetic study could be designed in consultation with representatives of the regulatory agency or government entity from whom approval is required before marketing the pharmacogenetic drug product in a particular country. Preferably, the regulatory agency is authorized by the government of a major industrialized country, such as Australia, Canada, China, a member of the European Union, Japan, and the like. Most preferably the regulatory agency is authorized by the government of the United States and the type of application for approval that is filed will depend on the legal requirements set forth in the last enacted version of the Food, Drug and Cosmetic Act that are applicable for the drug product and may also include other considerations such as the cost of making the regulatory filing and the marketing strategy for the drug product. For example, if the pharmaceutical formulation in the drug product has previously been approved for the disease component of the proposed pharmacogenetic indication, then the application might be a paper NDA, a supplemental NDA or an abbreviated NDA, but the application would might need to be a full NDA if the pharmaceutical formulation has never been approved before; with these terms having the meanings applied to them by those skilled in the pharmaceutical arts or as defined in the Drug Price Competition and Patent Term Restoration Act of 1984.

One desired outcome of a pharmacogenetic clinical trial using the IFN-α response markers of the invention is approval to market a drug product which comprises (1) an interferon alpha pharmaceutical composition and (2) prescribing information which includes a pharmacogenetic indication for which the pharmaceutical composition is recommended. Prescribing information is typically found in the product insert, also frequently referred to as the package insert or label, for the drug.

As discussed above, the pharmacogenetic indication has two components: a disease component and an IFN-α response marker component. Thus, the prescribing information would describe a genetically defined groups of patients for which the drug has demonstrated efficacy for one or more diseases, symptoms or medical conditions. In some embodiments, the prescribing information will discuss how to identify individuals who are in the genetically defined group. For example, in some embodiments, the prescribing information states that the drug is indicated for individuals who test positive for one or more of the IFN-α response markers described herein. Alternately, the prescribing information may state that the drug is contraindicated for individuals who test negative for one, more or all of these IFN-α response markers. In some preferred embodiments, the prescribing information includes the name of at least one approved diagnostic test to be used for detecting the presence or absence of the required genetic marker component of the pharmacogenetic indication. As described above, pharmacogenetic indication in a pharmacogenetic drug product of the invention may include additional markers or predictors of response to the IFN-α pharmaceutical composition and/or a requirement to use the drug in combination with one or more other therapeutically active agents. The prescribing information may include information on recommended dosages and treatment regimens.

In some embodiments, the pharmacogenetic drug product is provided as a formulation or in packaging that has a distinctive appearance that the manufacturer has adopted to identify the drug product as a pharmacogenetic product to aid pharmacists and physicians in distinguishing this product from other marketed products comprising the same or similar IFN-α active ingredient, but which do not have a pharmacogenetic indication. Using the appearance of pharmaceutical formulations and drug product packaging as part of creating a distinctive brand for drug products is well known in the art, and includes the shape and color of tablets or capsules, as well as symbols or logos stamped thereon, or on the packaging material for the drug product.

In preferred pharmacogenetic drug products of the invention, the pharmaceutical composition comprises a pegylated interferon alpha-2a, a pegylated interferon alpha-2b, or albinterferon alfa-2b. More preferably, the pharmaceutical composition comprises a bPEG40K-interferon alfa-2a or a PEG12k-interferon alfa-2b. A preferred pharmacogenetic indication for the drug products of the invention comprises the use of the pharmaceutical composition for the treatment of patients chronically infected with HCV genotype 1 and who test positive for at least one of the homozygous IFN-α, response markers described herein. In some preferred embodiments, the patients have a high baseline HCV viral load, as defined hereinabove. In more preferred embodiments, the prescribing information states that the interferon alpha pharmaceutical composition is indicated in combination with at least one other antiviral agent for treating patients chronically infected with a high baseline viral load of HCV genotype 1. The antiviral agent may be ribavirin, an HCV protease inhibitor, and HCV polymerase inhibitor, or another agent that specifically inhibits HCV replication. The prescribing information may recommend the use of the interferon alpha pharmaceutical composition in combination with any combination of two or more of these antiviral agents. In addition, the prescribing information may include a recommended treatment regimen, with preferred treatment regimens being any of those described above for PEG12k-interferon alfa-2b and bPEG40K-interferon alfa-2a pharmaceutical compositions.

Any or all analytical and mathematical operations involved in performing the methods described herein or in using the kits and products described herein may be implemented by a computer. For example, the computer may execute a computer program that assigns the presence or absence of an IFN-α response marker to an individual based on genotype data inputted by an employee of a testing laboratory or by the treating physician. In addition, the same computer or a different computer may output the predicted response to IFN-α therapy based on that response marker assignment. In some embodiments, the computer executes a computer program that derives a response probability score for the patient from various patient and disease parameters associated with IFN-α response, including the presence or absence of an IFN-α response marker. Data relating to the presence or absence of IFN-α markers in an individual may be stored as part of a relational database (e.g., an instance of an Oracle database or a set of ASCII flat files) containing other clinical and/or genetic data for the individual. These data may be stored on the computer's hard drive or may, for example, be stored on a CD ROM or on one or more other storage devices accessible by the computer. For example, the data may be stored on one or more databases in communication with the computer via a network.

EXAMPLES

The following examples are provided to more clearly describe the present invention and should not be construed to limit the scope of the invention.

Example 1

Quantitative RT-PCR Assay for HCV RNA

A Principle

The detection of HCV-RNA is determined by extracting total RNA from a biological sample and performing the reverse transcription-polymerase chain reaction (RT-PCR). The RT-PCR used is an automated method that allows for real-time quantitation of target nucleic acid molecules. This method utilizes the reverse transcriptase, 5'-exonuclease and DNA polymerase activities of the rTth DNA polymerase. The rTth DNA polymerase first makes DNA copies of the viral RNA (reverse transcriptase activity) and then proceeds to make copies of the DNA (polymerase activity). As the amplification proceeds, the 5'-exonuclease activity of rTth DNA polymerase digests a sequence-specific probe. This action releases a fluorescent signal allowing quantitation of the input RNA copies.

HCV genotype is determined by sequencing the PCR amplified DNA fragment of the 5'-untranslated region of the HCV genome. The sequence is then aligned with the published sequences of the HCV genotypes to arrive at a determination.

B Extraction of RNA from Sample

Total RNA is extracted in an automated high throughput liquid handler and QIAamp 96 Viral RNA extraction kit from QIAGEN (Germantown, Md.). This method gives high quality RNA suitable for RT-PCR.

Quantitative RT-PCR for HCV

One-step RT-PCR is performed using rTth DNA polymerase. Direct detection of the RT-PCR product is accomplished by monitoring the increase in fluorescence of the dye-labeled probe. During PCR, if the target of interest is present, the probe specifically anneals to the target. The 5'-exonuclease activity of the rTth DNA polymerase digests the probe releasing fluorescence. This process occurs in every cycle during PCR and does not interfere with the exponential accumulation of product. The increase in fluorescence (proportional to the amount of PCR product accumulated) is detected only if the target sequence is complementary to the probe and is amplified during PCR. Because of these requirements, nonspecific amplification is not detected.

The system is able to measure PCR products after every cycle of amplification. Initial copy number of the target template is determined by analyzing the cycle-to-cycle change in fluorescence signal (.Rn) as a result of the amplification of template during PCR. The fewer cycles it takes to reach a detectable level of fluorescence (reported as Ct, the threshold cycle), the greater the initial copy number. The Sequence Detection application determines initial copy numbers of unknowns by interpolation on a standard curve generated from standards of known initial copy number.

D Quality Control/Quality Assurance

An internal. RNA control is added to each sample to check efficiency of RNA extraction and RT-PCR. Different dilutions of a precalibrated HCV control RNA is run in every assay to generate a standard curve. HCV Proficiency Panel Members are run with each assay as positive controls. Normal human sera and water are run as negative control for RNA extraction and RT-PCR.

RT-PCR HCV-RNA determinations performed using the above assay have been validated against WHO International Standards for hepatitis C virus RNA and the HCV Panel from Acro Metrix. The lower limit of quantitation for this assay is 29 international units/mL (IU/mL). All HCV-RNA results reported herein are in IU/mL.

Example 2

Identification of a Single Nucleotide Polymorphism (SNP) Associated with HCV Response to Treatment with Peginterferon Alfa 2/Ribavirin Combination Therapy In order to identify genetic contributions to treatment response, the inventors carried out a genome-wide association study on genomic samples obtained from two prospective clinical studies. Over 1500 individuals were part of the IDEAL study, the design of which was reported in McHutchinson et al., *J. Viral Hepatol.*, Vol. 15, No. 7, July 2008, pp. 475-481). In order to increase the number of African Americans in the genome wide association analysis, 67 patients were also included from another prospective study focused on treatment of African Americans with peginterferon alfa-2b and ribavirin (Muir, A. J., Bornstein, J. D. & Killenberg, P. G. Peginterferon alfa-2b and ribavirin for the treatment of chronic hepatitis C in blacks and non-Hispanic whites. *N Engl J Med* 350, 2265-71 (2004)).

Briefly, in the IDEAL study, treatment-naive patients chronically infected with HCV genotype 1 were randomized (1:1:1) to receive one of the following 48-week treatment regimens: peginterferon alfa-2b (PEG2b) at 1.5 mcg/kg/week plus ribavirin (RBV); PEG2b at 1.0 mcg/kg/week plus RBV; or peginterferon alfa-2a (PEG2a) at 180 mcg/week RBV. In the PEG2b regimens, patients weighing 40-65 kg received 800 mg/day RBV; patients weighing more than 65 and up to 85 kg received 1000 mg/day RBV; patients weighing more than 85 and up to 105 kg received 1200 mg/day RBV; and patients weighing more than 105 kg received 1400 mg/day RBV). In the PEG2a regimen patients weighing <75 kg received 1000 mg/day of RBV while patients weighing $\geq$75 kg received 1200 mg/day of RBV. HCV RNA status was determined at baseline, at 12 and 24 weeks of treatment, at the end of 48 weeks treatment and at 24 weeks following treatment. Subjects with insufficient viral response at 12 or 24 weeks discontinued therapy as treatment failures. The results of the IDEAL study demonstrated essentially equivalent efficacy of the PEG2b (1.5 mcg/kg/week) plus RBV and the PEG2a regimens, with a significantly lower response in well-matched African Americans compared to Caucasians.

All patients included in the genome wide analysis were treatment naïve and chronically infected with genotype 1 HCV. Patients received 48 weeks of treatment (subjects with insufficient viral response at 12 or 24 weeks discontinued therapy per protocol as treatment failures) and 24 weeks of follow-up. Genomic samples from 1630 individuals were genotyped using the Human610-quad BeadChip from Illumina® (San Diego, Calif.), which contains about 600,000 tagging SNPs derived from phase II HapMap data (HumanHap 610 quad V 1.0). The genotyping results were analyzed for determinants of treatment response (viral clearance or SVR) as a primary endpoint. Treatment response and non-response (NR) were defined according to standard definitions (Ghany, M. G. et al., Strader, D. B., Thomas, D. L. & Scoff, L. B. American Association for the Study of Liver Diseases: Practice Guidelines; Diagnosis, Management, and Treatment of Hepatitis C: An Update. (2009)). Sustained virological response was defined as undetectable serum HCV RNA using a sensitive RT-PCR assay 24 weeks after cessation of treatment (or undetectable viral levels at 12 weeks follow-up if no further follow up was available). Non-response was defined either as a failure to achieve at least a 2-$\log_{10}$ reduction in serum HCV RNA at week 12 of treatment, or as detectable serum HCV RNA at the end of follow-up. All patients who achieved an SVR were included in the analysis as responders. In order to ensure that only non-responders with adequate drug exposure were evaluated (true biological non-responders), only patients with a minimum of 12 weeks of therapy and compliance of greater than 80% for both PegIFN and RBV were included in the association analyses. A series of quality control procedures were applied to ensure the data quality. A total of 1,143 hepatitis C patients with sufficient treatment response data fulfilled these criteria, and were then included in the association analyses (Table 3).

The primary association tests on SVR involved single-marker genotype trend tests performed in three independent ethnic populations (Caucasians, N=874; African Americans, N=191; and Hispanics, N=78), using logistic regression models implemented in the PLINK software (Purcell, S. et al. *Am J Hum Genet.* 81 (2007)) with corrections for a number of clinical covariates, including baseline (pre-treatment) serum HCV viral load and fibrosis severity.

TABLE 3

Clinical characteristics of the hepatitis C populations for studying SVR

| | Populations | | |
|---|---|---|---|
| | Caucasians | African Americans | Hispanics |
| N | 874 | 191 | 78 |
| Sex (F/M) | 332/542 | 71/120 | 30/48 |
| Age (yrs) | 47.5 (7.2) | 50.1 (6.5) | 45.3 (9.1) |
| BMI (kg/m$^2$) | 28.0 (4.4) | 29.9 (4.8) | 29.3 (5.5) |
| Baseline viral load ($\log_{10}$ IU/mL) | 6.4 (0.6) | 6.3 (0.5) | 6.2 (0.7) |
| Baseline liver fibrosis stage (n, %) | | | |
| Minimal (F0-2) | 773 (88.4%) | 174 (91.1%) | 66 (84.6%) |
| Advanced (F3-4) | 101 (11.6%) | 17 (8.9%) | 12 (15.4%) |
| SVR/NR (SVR %) | 490/384 (56.1%) | 45/146 (23.6%) | 40/38 (51.3%) |

SVR, sustained virological response (SVR24 = 539, SVR12 = 36); NR, Non-response; BMI, body mass index. Basal viral load is logarithmically transformed. Fibrosis was scored by METAVTR stage on a baseline centrally evaluated liver biopsy *Hepatology* 20, 15-20 (1994); McHutchison, J. G. et al. *N Engl J Med.* In press (2009). Data re mean (SD) unless otherwise indicated.

Then the association signals (P values) were combined using the Stouffer's weighted Z-method (Whitlock, M. C., et al. *J Evol Biol* 18, 1368-73 (2005)), correctly taking into account sample sizes, effect sizes, and effect directions in each population. This combined P value was then reported as the main result, along with the P values in each ethnic population. A series of quality control steps resulted in 565,759 polymorphisms for the association tests. Methods were applied to assess copy number variants (CNV) and tested the relationship between CNVs and SVR. To control for the possibility of spurious associations resulting from population stratification, a modified EIGENSTRAT method (Price, A. L. et al. *Nat Genet* 38, 904-9 (2006)) was used to correct for population ancestry axes within each ethnic population. Significance was assessed with a Bonferroni correction (P cut-off=$2.9 \times 10^{-8}$).

These analyses showed that a polymorphism on chromosome 19, rs12979860, is strongly associated with. SVR in all patient groups studied, with the Caucasian patient group showing overwhelming genome-wide significance (P=$1.17 \times 10^{-25}$). Combining the p values across the population groups the variant shows association at $1.21 \times 10^{-28}$ (FIG. 1 and Table 4).

TABLE 4

Results of the GWAS on HCV treatment induced clearance in individual and combined Hepatitis C populations

| | SVR | |
|---|---|---|
| | N | P value |
| Caucasians | 874 | $1.17 \times 10^{-25}$ |
| African Americans | 191 | $2.07 \times 10^{-3}$ |
| Hispanics | 78 | $2.52 \times 10^{-3}$ |
| Combined | 1143 | $1.21 \times 10^{-28}$ * |

* Effects were consistent in direction and P values were combined using the Stouffer's weight Z-method[2].

Figure 2:
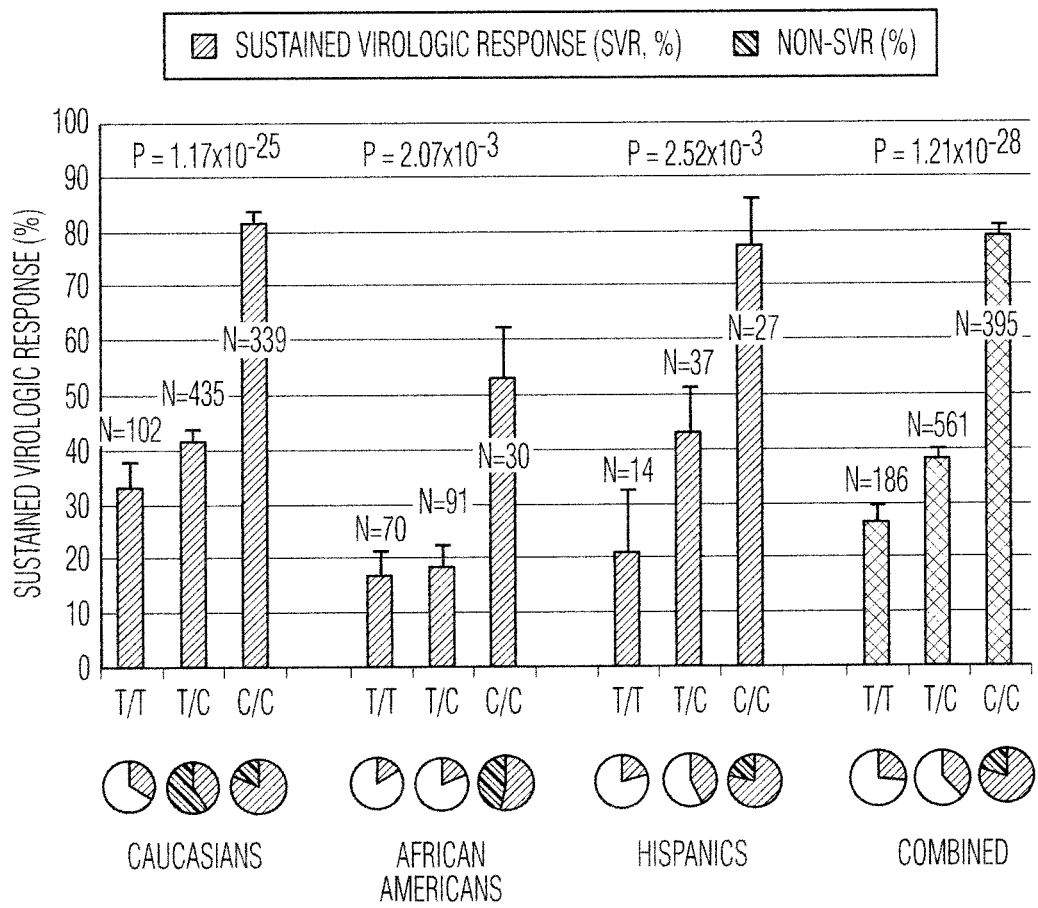
FIG. 2 illustrates the association between genotype at the rs12979860 polymorphic site (T/T, T/C or C/C) (Y-axis) and the percentage of patients with each genotype who achieved SVR (X-axis and pie charts) in different patient groups chronically infected with HCV genotype 1 and treated with peginterferon alfa/ribavirin combination therapy. Further details are in the Examples.

In the Caucasian patient group, the CC genotype is associated with a 2-fold greater rate of SVR than the TT genotype (FIG. 2), with similar ratios in both the African American (3-fold) and Hispanic patient groups (2-fold). Significantly, while there was a 2.4 fold difference in SVR rates in Caucasian and African American individuals grouped only by self-reported ethnicity (56.1%/23.6%), this variability dropped to a 1.5 fold difference between Caucasian and African Americans groups who had the C/C genotype (81.7%/53.3%). The inventors estimate that a significant amount of the lower SVR rates in African American patients is explained by the difference in frequency of the C allele in African American and Caucasian patient groups: 0.395 vs. 0.635, respectively. (FIG. 2, Table 5 below).

Figure 3:
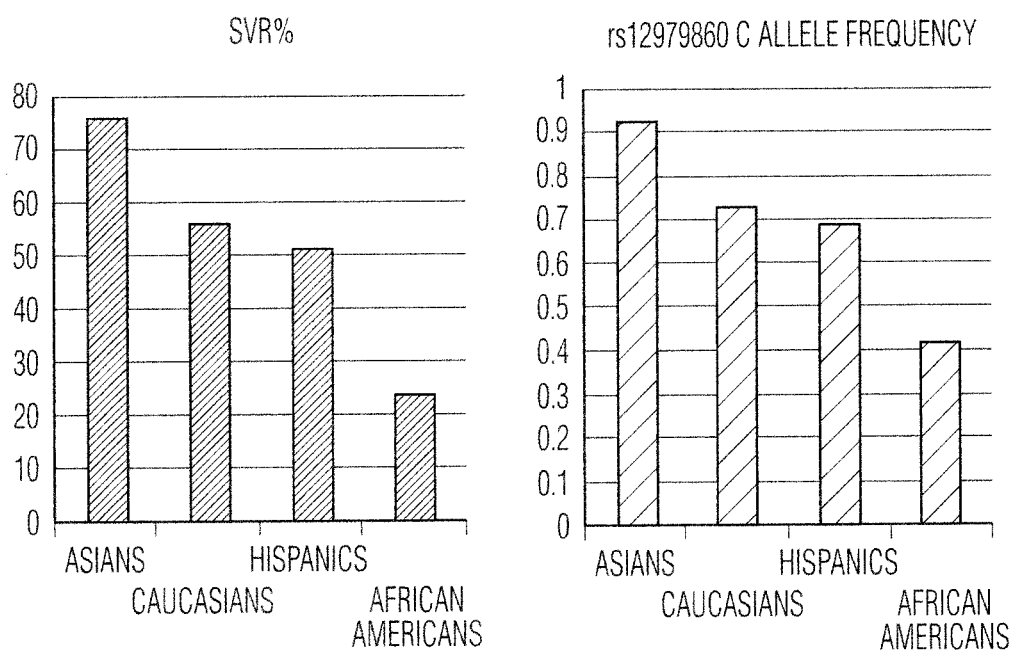
FIG. 3 illustrates the rate of sustained virological response (SVR) and rs12979860 C allele frequency in diverse ethnic groups, with the SVR rate in Caucasians, Hispanics and African Americans taken from the two clinical studies described in the Examples herein and the SVR rate in East Asians adopted from Liu, C. H. et al., Pegylated interferon-alpha-2a plus ribavirin for treatment-naive Asian patients with hepatitis C virus genotype 1 infection: a multicenter, randomized controlled trial. *Clin Infect Dis* 47, 1260-9 (2008). Further details are in the Examples.

Interestingly, it has been well documented that East Asians have higher SVR rates than Caucasians (Liu, C. H., et al. *Clin Infect Dis* 47, 1260-9 (2008); Yan, K. K. et al., *World J Gastroenterol* 14, 3416-20 (2008)). By looking at a random multi-ethnic population sample with unknown hepatitis C status, we observed a substantially higher frequency of the C allele in East Asians (FIG. 3). Collectively, as showed in FIG. 3, the SVR rates across diverse ethnic groups displayed a striking concordance between C allele frequency and estimate SVR rates of drug response in each group.

Finally, it is also noteworthy that African Americans with the CC genotype have a significantly higher rate of response (53.3%) than individuals of European ancestry that have the TT genotype (33.3%, p<0.05), emphasizing the importance of individual genotype over ethnicity in predicting treatment response (Wilson, J. F. et al. Population genetic structure of variable drug response. *Nat Genet* 29, 265-9 (2001)).

Example 3

Identification of Candidate Causal Variants Responsible for Variability in SVR

In an effort to identify the causal variant or variants responsible for these associations, we first tested for association between the rs12979860 SNP and gene expression in peripheral blood mononucleated cells from 80 individuals (uninfected population controls) in the SNPExpress database, which relates a genome-wide set of polymorphisms to genome-wide expression patterns in two primary populations of cells (Heinzen, E. L. et al. Tissue-specific genetic control of splicing: implications for the study of complex traits. *PLoS Biol* 6, el (2008)). We found no correlation with expression levels of IL28B with the best proxy for rs12979860 available in this database (rs12980275, $r^2$=0.88 with rs12979860), although IL28B expression levels in the absence of infection were low. Additional studies are needed to evaluate the effect of rs12979860 on IL28B expression in the presence of HCV infection, and more specifically in HCV-infected hepatocytes.

Six other SNPs in the same genomic region as rs12979860 had genome-significant association signals on the Illumina Human610-quad BeadChip (rs12980275, rs8099917, rs12972991, rs8109886, rs4803223, rs12980602, Table 1). These SNPs are possible candidates for being responsible for this association, but the association signals of these SNPs can be largely explained by the signal of rs12979860, because of the linkage disequilibrium between each of these SNPs and rs12979860, as shown in Table 4A below.

TABLE 4A

SNPs in the IL28B region showing genome-wide association with SVR

| SNP | P | Caucasians $r^2$ | Caucasians D' | African Americans $r^2$ | African Americans D' | Hispanics $r^2$ | Hispanics D' |
|---|---|---|---|---|---|---|---|
| rs12979860 | $1.21 \times 10^{-28}$ | — | — | — | — | — | — |
| rs12980275 | $2.82 \times 10^{-27}$ | 0.88 | 0.96 | 0.56 | 0.90 | 0.88 | 1.00 |
| rs8099917 | $4.37 \times 10^{-26}$ | 0.52 | 0.99 | 0.07 | 1.00 | 0.78 | 1.00 |
| rs12972991 | $1.88 \times 10^{-21}$ | 0.63 | 0.96 | 0.08 | 1.00 | 0.78 | 1.00 |
| rs8109886 | $1.32 \times 10^{-18}$ | 0.61 | 1.00 | 0.38 | 0.97 | 0.77 | 1.00 |
| rs4803223 | $7.87 \times 10^{-16}$ | 0.26 | 0.80 | 0.04 | 0.82 | 0.66 | 0.90 |
| rs12980602 | $5.94 \times 10^{-9}$ | 0.15 | 0.50 | 0.01 | 0.22 | 0.52 | 0.72 |

Linkage disequilibrium measures (r2 and D') are between each SNP and rs12979860.

Due the proximity of rs12979860 to the IL-28B gene, all exons of the IL28B gene were sequenced in 96 samples. Two strongly associated putatively functional SNPs in the IL28B gene were: one amino acid replacement polymorphism at position 70 (Lys70Arg, or c.213A>G, or rs8103142), and one polymorphism in the promoter region (−37G>C, or rs28416813). Both SNPs are candidates for being responsible for this association and included in Table 1 too.

Example 4

Identification of Allele and Genotype Frequencies in HCV Patient Groups for SNPs Associated with SVR To estimate the prevalence of the C allele and the C/C genotype in chronically infected HCV patients and in the general population, the frequencies of the three possible genotypes for the rs12979860 PS were determined for all subjects used in the association analysis in Example 1 as well as in a random population sample of self-identified Caucasian individuals of unknown hepatitis C status, i.e., a Caucasian control population. These results are reported in Table 5 below.

TABLE 5

Allelic and Genotype Frequencies for the rs12979860 SNP

| Population | Number of Subjects | C Allele | C/C genotype | C/T genotype | T/T genotype |
|---|---|---|---|---|---|
| Caucasian Control | 263 | 0.732 | 0.513 | 0.437 | 0.049 |
| Caucasion HCV Patients | 876 | 0.635 | 0.387 | 0.497 | 0.116 |
| African American HCV Patients | 191 | 0.395 | 0.157 | 0.476 | 0.366 |
| Hispanic HCV patients | 78 | 0.583 | 0.346 | 0.474 | 0.179 |

If the polymorphism has an influence on natural clearance, then one would expect a frequency difference in this comparison, since all individuals who naturally clear the virus will be excluded from the chronic infection cohort. The data in Table 2 is consistent with that expectation, as there was a statistically significant different in the frequency of the C alleles in Caucasian individuals in the HCV cohort (0.635) and in the ethnically matched control population of unknown HCV status (0.732) (P=2.48×10⁻⁶). These data indicate that individuals with the C allele are preferentially excluded from the HCV cohort. This comparison shows that the rs12979860 C allele, associated with better response to treatment, is also associated with a greater likelihood of natural clearance of hepatitis C, although the magnitude of this effect is difficult to estimate absent a more direct comparison between a cohort known to naturally clear the virus and a similarly matched chronically infected one.

The allele frequencies for the two SNPs in the IL28B gene are as follows:
rs28416813
−37G>C: minus strand has reference allele G, which is associated with SVR
−37C allele frequency=0.345, in n=55 whites
−37C allele frequency=0.500, in n=11 blacks
G allele is associated with SVR
rs8103142
c.213A>G: minus strand has reference allele A, which is associated with SVR
Lys70Arg (reference allele c.213A codes for Lys70)
Arg70 allele frequency=0.361, in n=54 whites
Arg70 allele frequency=0.545, in n=11 blacks
A allele (Lys70) is associated with SVR Example 5

Linkage Disequilibrium Between Various SNPs Associated with SVR

LD Measure in Whites:
rs28416813 (−37G>C) with rs8103142 (213A>G): r-sq=0.96; D'=1.00
rs28416813 (−37G>C) with:
rs12979860: r-sq=1.00; D'=1.00
rs12980275: r-sq=0.88; D'=1.00
rs8099917: r-sq=0.50; D'=1.00
rs12972991: r-sq=0.59; D'=1.00
rs8109886: r-sq=0.49; D'=1.00
rs4803223: r-sq=0.08; D'=0.45
rs12980602: r-sq=0.19; D'=0.60
rs8103142 (213A>G) with:
rs12979860: r-sq=0.96; D'=1.00
rs12980275: r-sq=0.85; D'=1.00
rs8099917: r-sq=0.48; D'=1.00
rs12972991: r-sq=0.56; D'=1.00
rs8109886: r-sq=0.51; D'=1.00
rs4803223: r-sq=0.07; D'=0.42
rs12980602: r-sq=0.29; D'=0.65
LD measure in blacks (preliminary due to small sample size, n=11):
rs28416813 (−37G>C) with rs8103142 (213A>G): r-sq 0.83; D'=1.00
rs28416813 (−37G>C) with:
rs12979860: r-sq=0.69; D'=1.00
rs12980275: r-sq=0.83; D'=1.00
rs8099917: r-sq=0.22; D'=1.00
rs12972991: r-sq=0.16; D'=1.00
rs8109886: r-sq=0.38; D'=1.00
rs4803223: r-sq=0.10; D'=1.00
rs12980602: r-sq=0.18; D'=0.61
rs8103142 (213A>G) with:
rs12979860: r-sq=0.83; D'=1.00
rs12980275: r-sq=0.69; D'=1.00
rs8099917: r-sq=0.19; D'=1.00
rs12972991: r-sq=0.13; D'=1.00
rs8109886: r-sq=0.45; D'=1.00
rs4803223: r-sq=0.12; D'=1.00
rs12980602: r-sq=0.23; D'=0.64

Example 6

Comparison of the Genetic and Clinical Predictors of SVR

To quantitatively compare the magnitude of different predictors of response for the patients studied here, the inventors developed a simple logistic regression model which relates several known clinical predictors, as well as the rs12979860 genotype, to response rates.

$$P = \frac{1}{1 + e^{-[(1.4 \times G)+(1.7 \times V)+(1.1 \times E)+(1.1 \times F)-3.8]}},$$

where
P: Probability of achieving SVR;
G: rs12979860 genotype: TT=0, CT=1, CC=2;
V: Baseline viral load: >600,000 IU/mL=0, <600,000 IU/mL=1;
E: Ethnicity: African Ancestry=0, Caucasian=1;
F: Baseline fibrosis: METAVIR F3-4=0, F0-2=1
This regression model shows that the CC genotype is associated with a more substantial difference in rate of response than the other known baseline predictors included in the model.

Example 7

The rs12979860 Polymorphism is Associated with Spontaneous Viral Clearance

The inventors tested whether the rs12979860 polymorphism influences natural clearance of hepatitis C by comparing allele frequencies in the chronically infected patients in this study (Table 3 above) to a random multi-ethnic population sample of apparently healthy individuals with unknown hepatitis C status. All subjects signed informed consent to participate in genetic studies. They were genotyped using the Illumina Human 610-Quad BeadChip and the genotype data were subject to quality control procedures as described for the HCV cohort. Table 6 below shows the general characteristics of this population sample.

TABLE 6

General characteristics of the random multi-ethnic population sample

| | Populations | | | |
|---|---|---|---|---|
| | Caucasians | African Americans | Hispanics | East Asians |
| N | 271 | 61 | 16 | 107 |
| Sex (F/M) | 141/130 | 41/20 | 7/9 | 59/48 |
| Age (yrs) | 23.5 (7.4) | 28.5 (12.2) | 23.3 (6.8) | 21.1 (2.6) |

Data are mean (SD) unless otherwise indicated. Ethnicity was self-reported by the participant.

If the rs12979860 polymorphism influences natural clearance one would expect a frequency difference in this comparison, since all individuals who naturally clear the virus will be excluded from the chronic infection cohort, thereby reducing the frequency of the allele that increases the likelihood of natural clearance. The inventors found that the frequency of the C allele was significantly reduced in the chronically infected cohort, with a frequency of 0.63 in individuals of European ancestry in the HCV cohort compared with a frequency of 0.732 in the ethnically matched controls that were corrected for any cryptic stratification (P=2.48×10⁻⁶), indicating that individuals with the C allele are preferentially excluded from the HCV cohort. This comparison shows that the rs12979860 C allele, associated with better response to treatment, is also associated with a greater likelihood of natural clearance of hepatitis C. The magnitude of the effect is difficult to estimate absent a more direct comparison between a cohort known to naturally clear the virus and a similarly matched chronically infected one.

Example 8

The IFN-λ3 Arg70 Isoform is Unstable when Expressed in Bacteria

To assess if the G allele of the rs8103142 SNP affects the expression or function of the IFN-λ3 Arg7O isoform, His-tagged IFN-λ3 Lys7O and His-tagged IFN-3 Arg7O isoforms expressed in bacteria cells were purified and the antiviral activity of each purified isoform was assessed using an EMCV virus challenge assay. Surprisingly, extensive degradation of the Arg isoform, but not the Lys isoform, was observed during purification, but comparable antiviral activity was observed when equivalent amounts of the full-length, purified isoforms were used.

Example 9

Reduced Secretion of the IFN-λ3 Arg70 Isoform Relative to the IFN-λ3 Lys70 Isoform from Human 293T Cells To assess whether the IFN-λ3 Arg70 isoform is also unstable when expressed in human cells the following experiment was performed.

Mammalian Expression Constructs:

IFN-λ3 Lys70 isoform and IFN-λ3 Arg70 isoform gene sequences, in which DNA coding sequences for the myc antibody epitope were incorporated at the 3' terminus of the IFN-λ3 gene coding sequences, were synthesized in vitro (GenSript, Piscataway, N.J.). The resulting IFN-λ3-myc tag gene coding regions were incorporated into the mammalian expression vector pCDNA3.1 (+) (Invitrogen, Carlsbad, Calif.), by standard restriction enzyme digest and ligation, so that IFN-λ3 gene expression was regulated by the early cytomegalovirus (CMV) enhancer/promoter. The resulting constructs were named pcDNA3.1 (+) IFN-λ3 Lys70 and pcDNA3.1 (+) IFN-2.3 Arg70.

Detection of Expressed IFN-λ3 Proteins:

293T cells (CRL-11268) were purchased from ATCC (Manassas, Va.) and maintained in DMEM supplemented with 10% FBS and 300 µg/ml G418. For detection of IFN-λ3 expression, 3×10⁶ 293T cells were plated onto 100 min cell culture dishes (Corning, Corning, N.Y.) and 24 hours later 10 µg of pcDNA3.1(+)IFN-λ3 Lys70 or pcDNA3.1(+)IFN-λ3 Arg70 plasmid was transfected by the calcium phosphate method using ProFection® Mammalian Transfection system (Promega Corp., Madison, Wis.). At 48 hours after transfection cell supernatants were collected and equal volumes were separated on identical 10% NuPAGE bis-tris gels (Invitrogen, Carlsbad, Calif.). One of the NuPAGE gels was stained with Comassie Blue (Invitrogen, Carlsbad, Calif.) to confirm equal protein loading, and proteins from the other NuPAGE gel were transferred to PVDF membrane (Invitrogen, Carlsbad, Calif.). The PVDF membrane was then analyzed by Western blot with Anti-c-Myc (Ab-1) mouse monoclonal 9E10 antibody (Calbiochem, La Jolla, Calif.) for detection of the myc-tagged IFN-λ3 Lys70 and IFN-λ3 Arg70 isoforms.

As shown in FIG. 5, the secretion of the myc-tagged IFN-λ3 Arg70 isoform was much lower than the secretion of the myc-tagged IFN-λ3 Lys70 isoform. This difference was quantified by measuring the intensity of the gel bands for each isoform. The total intensity for the Lys70 isoform was 9441, while for the Arg70 isoform it was only 2541, a fold reduction of 3.72. This result is consistent with the hypothesis that the G allele of the rs8103142 SNP is causally involved in the reduced response of HCV patients to peginterferon alfa-2b/ribavirin combination therapy.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Patents, patent applications, publications, product descriptions, and protocols are cited throughout this application, the disclosures of which are incorporated herein by reference in their entireties for all purposes.

We claim:

1. A method of testing an individual having a chronic infection with a hepatitis C virus (HCV) for the presence or absence of at least one IFN-α response marker in Table 1 below,

| PS | SNP | Better Response Allele | Heterozygous IFN-α Response Marker | Homozygous IFN-α Response Marker |
|---|---|---|---|---|
| rs12979860 | T/C | C | C/T genotype | C/C genotype |
| rs28416813 | G/C | G | G/C genotype | G/G genotype |
| rs8103142 | A/G | A | A/G genotype | A/A genotype |
| rs12980275 | A/G | A | A/G genotype | A/A genotype |
| rs8099917 | A/C | A | A/C genotype | A/A genotype |
| rs12972991 | T/G | T | T/G genotype | T/T genotype |
| rs8109886 | A/C | C | C/A genotype | C/C genotype |
| rs4803223 | T/C | T | T/C genotype | T/T genotype |
| rs12980602 | A/G | A | A/G genotype | A/A genotype | the method comprising obtaining a nucleic acid sample from the individual and assaying the nucleic acid sample to determine the individual's genotype at a polymorphic site (PS) in Table 1, wherein if the individual is heterozygous or homozygous for the better response allele for said PS, then the IFN-α response marker is present and if the individual is homozygous for the other allele for said PS, then the IFN-α response marker is absent.

2. The method of claim 1, which further comprises generating a test report that indicates the individual's genotype at said PS.

3. The method of claim 1, wherein the IFN-α response marker is selected from the homozygous IFN-α response marker genotypes in Table 1.

4. The method of claim 3, wherein the polymorphic site is rs12979860, rs28416813 or rs8103142 and the assaying step comprises amplifying from the nucleic acid sample a target region containing the PS and assaying the amplified target region to determine the identity of the pair of alleles at the PS.

5. The method of claim 1, wherein the hepatitis C virus is HCV genotype 1.

6. The method of claim 1, wherein IFN-α response marker is homozygous C at rs12979860.

7. The method of claim 6, further comprising assaying the nucleic acid sample to determine the individual's genotype at each of rs28416813 and rs8103142.

* * * * *